United States Patent
Gruetzmacher et al.

(10) Patent No.: US 9,701,700 B2
(45) Date of Patent: Jul. 11, 2017

(54) PROCESS FOR THE PREPARATION OF ACYLPHOSPHANES

(71) Applicant: ETH ZÜRICH, Zürich (CH)

(72) Inventors: Hansjoerg Gruetzmacher, Dielsdorf (CH); Georgina Mueller, Zurich (CH)

(73) Assignee: ETH ZUERICH, Zurich (CH)

( * ) Notice: Subject to any disclaimer, the term of this patent is extended or adjusted under 35 U.S.C. 154(b) by 0 days.

(21) Appl. No.: 14/432,212

(22) PCT Filed: Sep. 30, 2013

(86) PCT No.: PCT/EP2013/070378
§ 371 (c)(1),
(2) Date: Mar. 30, 2015

(87) PCT Pub. No.: WO2014/053455
PCT Pub. Date: Apr. 10, 2014

(65) Prior Publication Data
US 2015/0299231 A1    Oct. 22, 2015

(30) Foreign Application Priority Data

Oct. 1, 2012 (EP) .................. 12006822
Jul. 18, 2013 (EP) .................. 13003616

(51) Int. Cl.
| | | |
|---|---|---|
| C08F 112/08 | (2006.01) | |
| C08F 2/50 | (2006.01) | |
| C08F 218/08 | (2006.01) | |
| C08F 230/08 | (2006.01) | |
| C07F 9/655 | (2006.01) | |
| C07F 9/53 | (2006.01) | |
| C07F 9/50 | (2006.01) | |
| C07F 9/572 | (2006.01) | |
| C07F 9/58 | (2006.01) | |

(52) U.S. Cl.
CPC ........ *C07F 9/65515* (2013.01); *C07F 9/5036* (2013.01); *C07F 9/5072* (2013.01); *C07F 9/5337* (2013.01); *C07F 9/572* (2013.01); *C07F 9/582* (2013.01); *C08F 2/50* (2013.01); *C08F 218/08* (2013.01)

(58) Field of Classification Search
None
See application file for complete search history.

(56) References Cited

U.S. PATENT DOCUMENTS

2004/0248855 A1   12/2004   Leppard et al.
2006/0247436 A1   11/2006   Sommerlade et al.
2008/0004464 A1 *  1/2008   Murer .................. C07F 9/5036
                                                  560/51
2008/0071115 A1    3/2008   Sommerlade et al.
2012/0142805 A1    6/2012   Grutzmacher et al.

FOREIGN PATENT DOCUMENTS

| EP | 1 135 399 B1 | 9/2001 |
|---|---|---|
| WO | WO 2005/014605 A1 | 2/2005 |
| WO | WO 2006/056541 A1 | 6/2006 |
| WO | WO 2006/074983 A1 | 7/2006 |
| WO | WO 2011/003772 A1 | 1/2011 |

OTHER PUBLICATIONS

Issleib & Malotki, 3(4) Phosphorus & the Related Group V Elements, 141-52 (1973) (CAS Abstract).*
K. Sasse: "3. durch Anlagerung an Kohlenstoff-Kohlenstoff-Doppelbindungen", Metiioden Der Organisciien Ciiemie, vol. 12, Englisch Abstract, pp. 25-28 (1963).
R. G. Kostyanovskii et al.: "Geminal Systems. 19 Reactions of Aminomethylphosphines With Electrophilic Reagents", Academy of Sciences of the USSR, vol. 31, No. 7, pp. 1433-1441 (1982).
V. K. Khairullin et al.: "Synthesis and Properties of 2-Ethyl-1-Butyl-5-OXO-1,2-Azapiiospholane", Academy of Sciences of the USSR, vol. 21, No. 9, pp. 1997-2000 (1972).
S. Jockusch et al.: "Phosphinoyl Radicals: Structure and Reactivity. A Laser Flash Photolysis and Time-Resolved ESR Investigation", J. Am. Chem. Soc., vol. 120, pp. 11773-11777 (1998).
E. Lindner et al.: "Bifunctional Acyl(diorganyl)phosphanes and their Behavior Towards Molecular Oxygen", Z. Naturforsch, vol. 33B, No. 12, English Abstract, pp. 1457-1460 (1978).
J. Podlahová et al.: "Oxidation of Ethylenediphosphinetetraacetate Anions", Collection Czechoslovak Chem. Commun., vol. 48, pp. 2604-2608 (1983).
H. Grützmacher et al.: "A Simple Straightforward Synthesis of Phenylphosphane and the Photoinitiator Bis(mesitoyl)phenylphosphane Oxide (IRGACURE 819)", Chimia, vol. 62, pp. 18-22 (2008).

* cited by examiner

*Primary Examiner* — Timothy R Rozof
(74) *Attorney, Agent, or Firm* — Norman B. Thot

(57) ABSTRACT

The present invention provides a process for the preparation of mono- and bisacylphosphanes based on formula (I):

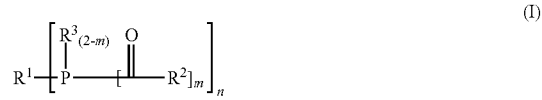

as well as for their corresponding oxides or sulfides. The present invention further relates to photoinitiators obtainable by said process.

9 Claims, No Drawings

PROCESS FOR THE PREPARATION OF ACYLPHOSPHANES

CROSS REFERENCE TO PRIOR APPLICATIONS

This application is a U.S. National Phase application under 35 U.S.C. §371 of International Application No. PCT/EP2013/070378, filed on Sep. 30, 2013 and which claims benefit to European Patent Application No. 12006822.6, filed on Oct. 1, 2012, and to European Patent Application No. 13003616.3, filed on Jul. 18, 2013. The International Application was published in English on Apr. 10, 2014 as WO 2014/053455 A1 under PCT Article 21(2).

FIELD

The present invention relates to a versatile, highly efficient process for the preparation of mono- and bisacylphosphanes, as well as for their corresponding oxides or sulfides. The present invention further relates to novel photoinitiators obtainable by said process.

BACKGROUND

Photoinitiators, in particular mono- and bisacylphosphane oxides, bearing further functionalized substituents, have attracted significant commercial attention since photoinitiators which are tunable with respect to the wavelength at which photoinduced cleavage occurs or which are linkable to other additives, such as sensitizers, stabilizers or surface active agents in order to avoid migration e.g., in food packaging, are highly desirable.

Many approaches to achieve these goals have been published during the last decade.

EP 1 135 399 A describes a process for the preparation of mono- and bisacylphosphanes and their respective oxides and sulfides the process comprising the steps of reacting substituted monohalophosphanes or dihalophosphanes with an alkali metal or a combination of magnesium and lithium, where appropriate in the presence of a catalyst, further reacting the resulting metallated phosphanes with carboxylic acid halides, and finally oxidizing the resulting mono- or bisacylphosphanes with sulfur or oxygen transferring oxidants.

WO05/014605A describes the preparation of bisacylphosphanes via a process comprising the steps of first reacting monohalophosphanes or dihalophosphanes with an alkali metal in a solvent in the presence of a proton source, and then reacting the phosphanes obtained thereby with carboxylic acid halides.

WO2006/056541A describes a process for the preparation of bisacylphosphanes, the process comprising the steps of reducing elemental phosphorous or phosphorous trihalides $P(Hal)_3$ with sodium to obtain sodium phosphide $Na_3P$, then adding sterically bulky alcohols to obtain sodium phosphide $NaPH_2$, reacting said sodium phosphide with two equivalents of an carboxylic acid halide to obtain sodium bisacylphosphides, and finally reacting said sodium bisacylphosphides with electrophilic agents to obtain bisacylphosphanes.

WO2006/074983A describes a process for the preparation of bisacylphosphanes by first catalytically reducing monochloro- or dichlorophosphines with hydrogen at a temperature of from 20 to 200° C. under pressure in the presence of a tertiary aliphatic amine or an aromatic amine in an aprotic solvent to obtain the corresponding halogen-free phosphanes, and subsequently reacting said phosphanes with carboxylic acid halides to obtain mono- or bisacylphosphanes.

However, for the variation of the non-acyl substituent(s) at the phosphorous atom the aforementioned processes either require the initial employment of an organic mono- or dihalophosphane already bearing such substituent(s) in a first reduction or metallation step, which significantly diminishes the variability of possible substitution patterns, or if e.g., sodium phosphides $NaPH_2$ are employed, the use of electrophilic compounds bearing a reactive halogen functionality at the substituent to be introduced, which renders such processes commercially less attractive.

SUMMARY

An aspect of the present invention is to provide an efficient and versatile process to prepare functionalized mono- or bisacylphosphanes an well as their respective oxides and sulfides.

In an embodiment, the present invention provides a process for the preparation of compounds of formula (I):

wherein,
n is an integer, for example, an integer from 1 to 6, for example, 1, 2, 3 or 4, for example, 1 or 2,
m is 1 or 2,
$R^1$, if n is 1 is a substituent of formula (IIa),

wherein,
(1) and (2) indicate the numeration of the carbon atom, whereby $C_{(1)}$ is bound to the central phosphorous atom depicted in formula (I), and
Z is a substituent selected from the group consisting of —CN, —$NO_2$, —(CO)H, —(CO)$R^8$, —(CO)OH, —(CO)$OR^8$, —(CO)$NH_2$, —(CO)NH($R^8$), —(CO)N($R^8$)$_2$, —($SO_2$)$R^8$, —(PO)($R^8$)$_2$, —(PO)($OR^8$)$_2$, —(PO)($OR^8$)($R^8$) or heteroaryl
$R^6$ and $R^7$ each substituent independently is hydrogen, Z or $R^8$ and
$R^8$ independently of further substituents $R^8$ which may be present in the substituent of formula (IIa) is alkyl, alkenyl or aryl or two substituents $R^8$ irrespective of whether they are both part of a substituent Z or belong to different substituents selected from Z, $R^6$ and $R^7$ together are alkanediyl or alkenediyl or alternatively, where two substituents —(CO)$R^8$ are present within the substituent of formulae (IIa), are together —O— or —$NR^4$—,
whereby the alkyl, alkenyl, aryl, alkanediyl and alkenediyl substituents are
either not, once, twice or more than twice interrupted by non-successive functional groups selected from the group consisting of:
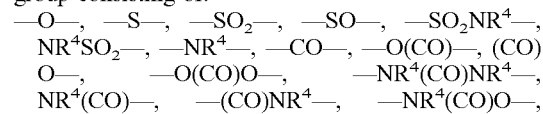

—O(CO)NR$^4$—, —Si(R$^5$)$_2$—, —OSi(R$^5$)$_2$—, —OSi(R$^5$)$_2$O—, —Si(R$^5$)$_2$O—, and either not, additionally or alternatively either once, twice or more than twice interrupted by bivalent residues selected from the group consisting of heterocyclo-diyl, and aryldiyl, and, either not, additionally or alternatively either once, twice or more than twice substituted by substituents selected from the group consisting of:

oxo, hydroxy, halogen, cyano, azido, $C_6$-$C_{14}$-aryl, $C_1$-$C_8$-alkoxy, $C_1$-$C_8$-alkylthio, —SO$_3$M, —COOM, PO$_3$M$_2$, —PO(N(R$^5$)$_2$)$_2$, PO(OR$^5$)$_2$, —SO$_2$N(R$^4$)$_2$, —N(R$^4$)$_2$, —CO$_2$N(R$^5$)$_2$, —COR$^4$, —OCOR$^4$, —NR$^4$(CO)R$^5$, —(CO)OR$^4$, —NR$^4$(CO)N(R$^4$)$_2$, —Si(OR$^5$)$_y$(R$^5$)$_{3-y}$, —OSi(OR$^5$)$_y$(R$^5$)$_{3-y}$ with y=1, 2 or 3, and, for example, also —N(R$^4$)$_3{}^+$An$^-$, or or R$^1$, if n is 1, is a substituent of formulae (IIb), (IIc) or (IId)

—C$_{(1)}$R$^6{}_2$—N(R$^8$)$_2$     (IIb)

—C$_{(1)}$R$^6{}_2$—NH(R$^8$)     (IIc)

—(C$_{(1)}$=O)—NHR$^8$     (IId)

wherein, (1) indicates the carbon atom bound to the central phosphorous atom depicted in formula (I) and R$^1$, if n is >1, in particular 2 to 6, for example, 2, 3 or 4 or, in another embodiment, 2, is a substituent of formula (IIe) or (IIf)

R*[C$_{(2)}$HR$^9$—C$_{(1)}$(R$^9$)$_2$—]$_n$     (IIe)

R**[NH—(C$_{(1)}$=O)—]$_n$     (IIf)

whereby in formula (IIe),

R* is either a divalent substituent selected from the group consisting of —CO— and —SO$_2$— (for n=2), or a n-valent substituent selected from the group consisting of heteroaryl-n-yl and R$^{10}$(-Het-(C=O)—)$_n$, wherein Het independently is either O or NR$^4$ and R$^{10}$ is alkane-n-yl, alkene-n-yl, or aryl-n-yl, and wherein the carbonyl carbons are bound to the C$_{(2)}$ carbon atoms, whereby the aforementioned alkane-n-yl and alkene-n-yl substituents of R$^{10}$ are either not, once, twice or more than twice interrupted by non-successive functional groups selected from the group consisting of:
—O—, —NR$^4$—, —CO—, —O(CO)—, —(CO)O—, NR$^4$(CO)—, —(CO)NR$^4$— and, either not, additionally or alternatively either once, twice or more than twice interrupted by aryldiyl, and, either not, additionally or alternatively either once, twice or more than twice substituted by substituents selected from the group consisting of:

hydroxy, $C_1$-$C_8$-alkoxy, —COOM, —N(R$^4$)$_2$, —CO$_2$N(R$^5$)$_2$, —COR$^4$, —OCOR$^4$, —NR$^4$(CO)R$^5$, —(CO)OR$^4$, (1) and (2) indicate the numeration of the carbon atom whereby each of the n C$_{(1)}$ carbon atoms is bonded to the central phosphorous atom depicted in formula (I) via the bond "—" shown on the right side of the bracket and R$^9$ independently of each other are hydrogen, alkyl, alkenyl or aryl or two substituents R$^9$ irrespective of whether they are both bound to C$_{(2)}$ or not are together alkanediyl or alkenediyl, whereby the aforementioned alkyl, alkenyl, alkane-n-yl and alkene-n-yl substituents of R$^9$ are either not, once, twice or more than twice interrupted by non-successive functional groups selected from the group consisting of:
—O—, —S—, —SO$_2$—, —SO—, —SO$_2$NR$^4$—, NR$^4$SO$_2$—, —NR$^4$—, —CO—, —O(CO)—, (CO)O—, —O(CO)O—, —NR$^4$(CO)NR$^4$—, NR$^4$(CO)—, —(CO)NR$^4$—, —NR$^4$(CO)O—, —O(CO)NR$^4$—, —Si(R$^5$)$_2$—, —OSi(R$^5$)$_2$—, —OSi(R$^5$)$_2$O—, —Si(R$^5$)$_2$O—, and, either not, additionally or alternatively either once, twice or more than twice interrupted by bivalent residues selected from the group consisting of heterocyclo-diyl, and aryldiyl, and, either not, additionally or alternatively either once, twice or more than twice substituted by substituents selected from the group consisting of:

oxo, hydroxy, halogen, cyano, azido, $C_6$-$C_{14}$-aryl, $C_1$-$C_8$-alkoxy, $C_1$-$C_8$-alkylthio, —SO$_3$M, —COOM, PO$_3$M$_2$, —PO(N(R$^5$)$_2$)$_2$, PO(OR$^5$)$_2$, —SO$_2$N(R$^4$)$_2$, —N(R$^4$)$_2$, —CO$_2$N(R$^5$)$_2$, —COR$^4$, —OCOR$^4$, —NR$^4$(CO)R$^5$, —(CO)OR$^4$, —NR$^4$(CO)N(R$^4$)$_2$, —Si(OR$^5$)$_y$(R$^5$)$_{3-y}$, —OSi(OR$^5$)$_y$(R$^5$)$_{3-y}$ with y=1, 2 or 3 and, for example, also —N(R$^4$)$_3{}^+$An$^-$, and whereby in formula (IIf)

R is a n-valent substituent selected from the group consisting of alkane-n-yl, alkene-n-yl and aryl-n-yl wherby R is bound to the nitrogen atoms, whereby the aforementioned alkane-n-yl and alkene-n-yl substituents are either not, once, twice or more than twice interrupted by non-successive functional groups selected from the group consisting of:
—O—, —NR$^4$—, —CO—, —O(CO)—, —(CO)O—, —NR$^4$(CO)—, —NR$^4$(CO)O—, —NR$^4$(CO) NR$^4$—, —(CO)NR$^4$— or isocyanurate, oxadiazintrione, uretdione, biuret or allophanate groups and, either not, additionally or alternatively either once, twice or more than twice interrupted by aryldiyl, and, either not, additionally or alternatively either once, twice or more than twice substituted by substituents selected from the group consisting of:

hydroxy, —NCO, $C_1$-$C_8$-alkoxy, —N(R$^4$)$_2$, —CO$_2$N(R$^5$)$_2$, —COR$^4$, —OCOR$^4$, —NR$^4$(CO)R$^5$, —(CO)OR$^4$, (1) indicates the numeration of the carbon atom whereby each of the n C$_{(1)}$ carbon atoms is bonded to the central phosphorous atom depicted in formula (I) via the bond "—" shown on the right side of the bracket, and R$^2$ and R$^3$, are independently of each other aryl or heterocyclyl, alkyl or alkenyl whereby the aforementioned alkyl and alkenyl substituents of R$^2$ and R$^3$ are either not, once, twice or more than twice interrupted by non-successive functional groups selected from the group consisting of:
—O—, —NR⁴—, —CO—, —OCO—, —O(CO)O—, NR⁴(CO)—, —NR⁴(CO)O—, O(CO)NR⁴—, —NR⁴(CO)NR⁴—,
and,
either not, additionally or alternatively either once, twice or more than twice interrupted by bivalent residues selected from the group consisting of heterocyclo-diyl, and aryldiyl,
and,
either not, additionally or alternatively either once, twice or more than twice substituted by substituents selected from the group consisting of:
oxo, hydroxyl, halogen, cyano, $C_6$-$C_{14}$-aryl; heterocyclyl, $C_1$-$C_8$-alkoxy, $C_1$-$C_8$-alkylthio, —COOM, —SO₃M, —PO₃M₂, —SO₂N(R⁴)₂, —NR⁴SO₂R⁵, —N(R⁴)₂—, —N⁺(R⁴)₃An⁻, —CO₂N(R⁴)₂, —COR⁴—, —OCOR⁵, —O(CO)OR⁵, NR⁴(CO)R⁴, —NR⁴(CO)OR⁴, O(CO)N(R⁴)₂, —NR⁴(CO)N(R⁴)₂,
whereby in all formulae where used,
R⁴ is independently selected from the group consisting of hydrogen, $C_1$-$C_8$-alkyl, $C_6$-$C_{14}$-aryl, and heterocyclyl or N(R⁴)₂ as a whole is a N-containing heterocycle,
R⁵ is independently selected from the group consisting of $C_1$-$C_8$-alkyl, $C_6$-$C_{14}$-aryl, and heterocyclyl or N(R⁵)₂ as a whole is a N-containing heterocycle,
M is hydrogen, or 1/q equivalent of an q-valent metal ion or is an ammonium ion or a guanidinium ion or a primary, secondary, tertiary or quarternary organic ammonium ion, in particular those of formula [N(C₁-C₁₈-alkyl)ₛHₜ]⁺, wherein s is 1, 2 or 3 and t is (4-s), and
An⁻ is 1/p equivalent of a p-valent anion,
the process comprising at least the step of reacting compounds of formula (III)

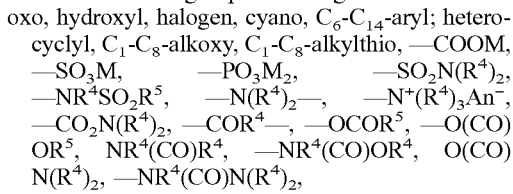

(III)

if n is 1
with compounds of formulae (IVa), (IVb), (IVc) or (IVd),

R⁶₂C₍₁₎═C₍₂₎(Z)(R⁷)   (IVa)

R⁶₂C₍₁₎═N⁺(R⁸)₂An⁻   (IVb)

R⁶₂C₍₁₎═NR⁸   (IVc)

R⁸—NCO   (IVd), if n is >1,
with compounds of formulae (IVe) or (IVf),

R*[R⁹C₍₂₎═C₍₁₎(R⁹)₂]ₙ   (IVe)

R**[NCO]ₙ   (IVf), wherein in formulae (III) and (IVa) to (IVf),
(1), (2), R², R³, R⁶, R⁷, R⁸, R⁹, R*, R**, n, m, An⁻ and Z have the same meaning as described for formulae (I) and (IIa) to (IIf) above, and
wherein in formula (II),
M² is hydrogen, or 1/q equivalent of an q-valent metal ion or is an ammonium ion or a heterocyclylium cation, a guanidinium ion or a primary, secondary, tertiary or quarternary organic ammonium ion, in particular those of formula [N(C₁-C₁₈-alkyl)ₛHₜ]⁺, wherein s is 1, 2 or 3 and t is (4-s), and
whereby the reaction if M² is hydrogen is carried out in the presence of a base.

DETAILED DESCRIPTION

In an embodiment, where M² is 1/q equivalent of an q-valent metal ion or a quarternary organic ammonium ion or a heterocyclylium cation, an acid, an acid with a pKa of 5 or less at 25° C. measured in water or an aqueous reference system can, for example, be added after the reaction to protonate the intermediates.

The compounds of formula (I) may be further functionalized by standard operations such as alkylations, nucleophilic substitutions, protonations with acids, deprotonations with bases, optionally followed by ion exchange and the like in order to obtain other compounds of formula (I).

Further details are given in the examples.

The scope of the present invention encompasses all combinations of substituent definitions, parameters and illustrations set forth above and below, either in general or within areas of examples or embodiments, with one another, i.e., also any combinations between the particular areas.

Whenever used herein the terms "including", "e.g.", "such as" and "like" are meant in the sense of "including but without being limited to" or "for example without limitation", respectively.

As used herein, and unless specifically stated otherwise, aryl denotes carbocyclic aromatic substituents, whereby said carbocyclic, aromatic substituents are unsubstituted or substituted by up to five identical or different substituents per cycle. The substituents can, for example, be selected from the group consisting of fluorine, bromine, chlorine, iodine, nitro, cyano, formyl or protected formyl, hydroxyl or protected hydroxyl, $C_1$-$C_8$-alkyl, $C_1$-$C_8$-haloalkyl, $C_1$-$C_8$-alkoxy, $C_1$-$C_8$-haloalkoxy, $C_6$-$C_{14}$-aryl, in particular phenyl and naphthyl, di($C_1$-$C_8$-alkyl)amino, ($C_1$-$C_8$-alkyl)amino, CO($C_1$-$C_8$-alkyl), OCO($C_1$-$C_8$-alkyl), NHCO($C_1$-$C_8$-alkyl), N($C_1$-$C_8$-alkyl)CO($C_1$-$C_8$-alkyl), CO($C_6$-$C_{14}$-aryl), OCO($C_6$-$C_{14}$-aryl), NHCO($C_6$-$C_{14}$-aryl), N($C_1$-$C_8$-alkyl)CO($C_6$-$C_{14}$-aryl), COO—($C_1$-$C_8$-alkyl), COO—($C_6$-$C_{14}$-aryl), CON($C_1$-$C_8$-alkyl)₂ or CONH($C_1$-$C_8$-alkyl), CO₂M, CONH₂, SO₂NH₂, SO₂N($C_1$-$C_8$-alkyl)₂, SO₃M, and PO₃M₂.

In an embodiment of the present invention, the carbocyclic, aromatic substituents can, for example, be unsubstituted or substituted by up to three identical or different substituents per cycle selected from the group consisting of fluorine, chlorine, cyano, $C_1$-$C_8$-alkyl, $C_1$-$C_8$-haloalkyl, $C_1$-$C_8$-alkoxy, $C_1$-$C_8$-haloalkoxy, $C_6$-$C_{14}$-aryl, in particular phenyl.

In an embodiment of present invention, the carbocyclic, aromatic substituents can, for example, be unsubstituted or substituted by up to three identical or different substituents per cycle selected from the group consisting of fluorine, $C_1$-$C_8$-alkyl, $C_1$-$C_8$-perfluoroalkyl, $C_1$-$C_8$-alkoxy, $C_1$-$C_8$-perfluoroalkoxy, and phenyl.

The definitions given above, including areas within examples, also apply analogously to aryldiyl and aryl-n-yl substituents. Aryl substituents can, for example, be $C_6$-$C_{14}$-aryl substituents, for example, phenyl, naphthyl, phenanthrenyl and anthracenyl. The term $C_6$-$C_{14}$ indicates that the number of carbon atoms of the respective carbocyclic, aromatic ring system is from 6 to 14. The possible and examples of substitution patterns mentioned above are likewise applicable.

As used herein and unless specifically stated otherwise, heterocyclyl denotes heterocyclic aliphatic, aromatic or mixed aliphatic and aromatic substituents in which no, one, two or three skeleton atoms per cycle, but at least one skeleton atom in the entire cyclic system is a heteroatom selected from the group consisting of nitrogen, sulphur and oxygen which are unsubstituted or substituted by up to five identical or different substituents per cycle, whereby the substituents are selected from the same group as given above for carbocyclic aromatic substituents including the areas of examples.

Heterocyclyl-substituents and heteroaryl-substituents respectively, can, for example, be pyridinyl, oxazolyl, thiophen-yl, benzofuranyl, benzothiophen-yl, dibenzofuranyl, dibenzothiophenyl, furanyl, indolyl, pyridazinyl, pyrazinyl, imidazolyl, pyrimidinyl and quinolinyl, either unsubstituted or substituted with one, two or three substituents selected from the group consisting of fluorine, $C_1$-$C_8$-alkyl, $C_1$-$C_8$-perfluoroalkyl, $C_1$-$C_8$-alkoxy, $C_1$-$C_8$-perfluoroalkoxy, and phenyl.

The definitions given above, including their example areas, also apply analogously to heterocyclylium and heteroarylium cations and the bivalent heterocyclo-diyl and heteroaryldiyl substituents.

Heterocyclylium cations can, for example, be N—($C_1$-$C_8$-alkyl)imidazolium or pyridinium cations.

As used herein, and unless specifically stated otherwise, protected formyl is a formyl substituent which is protected by conversion to an aminal, acetal or a mixed aminal acetal, whereby the aminals, acetals and mixed aminal acetals are either acyclic or cyclic.

Protected formyl is, for example, 1,1-(2,4-dioxycyclopentanediyl).

As used herein, and unless specifically stated otherwise, protected hydroxyl is a hydroxyl radical which is protected by conversion to a ketal, acetal or a mixed aminal acetal, whereby the aminals, acetals and mixed aminal acetals are either acyclic or cyclic. A specific example of protected hydroxyl is tetrahydropyranyl (O-THP).

As used herein, and unless specifically stated otherwise, alkyl, alkanediyl, alkenyl, alkenediyl, alkane-n-yl and alkene-n-yl are straight-chained, cyclic either in part or as a whole, branched or unbranched.

The term $C_1$-$C_{18}$-alkyl indicates that the straight-chained, cyclic either in part or as a whole, branched or unbranched alkyl substituent contains from 1 to 18 carbon atoms excluding the carbon atoms of optionally present substituents to the $C_1$-$C_{18}$-alkyl substituent. The same analogously applies to alkanediyl, alkenyl, alkenediyl, alkane-n-yl and alkene-n-yl and further substituents having an indicated number of carbon atoms.

For the avoidance of doubt, the term alkenyl denotes a substituent comprising at least one carbon-carbon double bond, irrespective of its location within the straight-chained, cyclic either in part or as a whole, branched or unbranched substituent.

Specific examples of $C_1$-$C_4$-alkyl are methyl, ethyl, n-propyl, isopropyl, n-butyl, tert-butyl. Additional examples for $C_1$-$C_8$-alkyl are n-pentyl, cyclohexyl, n-hexyl, n-heptyl, n-octyl, isooctyl. Additional examples for $C_1$-$C_{18}$-alkyl are norbornyl, adamantyl, n-decyl, n-dodecyl, n-hexadecyl, n-octadecyl.

Specific examples of $C_1$-$C_8$-alkanediyl-substituents are methylene, 1,1-ethylene, 1,2-ethylene, 1,1-propylene, 1,2-propylene, 1,3-propylene, 1,1-butylene, 1,2-butylene, 2,3-butylene and 1,4-butylene, 1,5-pentylene, 1,6-hexylene, 1,1-cyclohexylene, 1,4-cyclohexylene, 1,2-cyclohexylene and 1,8-octylene.

Specific examples of $C_1$-$C_4$-alkoxy-substituents are methoxy, ethoxy, isopropoxy, n-propoxy, n-butoxy and tert-butoxy. An additional example for $C_1$-$C_8$-alkoxy is cyclohexyloxy.

Specific examples of $C_2$-$C_{18}$-alkenyl and $C_2$-$C_8$-alkenyl-substituents are allyl, 3-propenyl and buten-2-yl.

As used above, $C_1$-$C_8$-haloalkyl and $C_1$-$C_8$-haloalkoxy are $C_1$-$C_8$-alkyl and $C_1$-$C_8$-alkoxy substituents which are once, more than once or fully substituted by halogen atoms. Substituents which are fully substituted by fluorine are referred to as $C_1$-$C_8$-perfluoroalkyl and $C_1$-$C_8$-perfluoroalkoxy, respectively.

Specific examples of $C_1$-$C_8$-haloalkyl-substituents are trifluoromethyl, 2,2,2-trifluoroethyl, chloromethyl, fluoromethyl, bromomethyl, 2-bromoethyl, 2-chloroethyl, nonafluorobutyl and n-perfluorooctyl.

The process according to the present invention requires employment of compounds of formula (III). Such compounds may be prepared in any manner known per se, for example, by the steps of:

A) contacting elemental phosphorous with a alkali or alkaline earth metal optionally in the presence of a catalyst or an activator in a solvent to obtain metal phosphides $M^3{}_3P$, wherein $M^3$ is an alkali or ½ equivalent of an alkaline earth metal, whereby the phosphides are usually present in a polymeric form and are therefore occasionally referred to as pholyphosphides, B) optionally adding a proton source, optionally in the presence of a catalyst or an activator to obtain metal dihydrogen phosphides $M^3PH_2$ which may depending on the proton source exist as complexes, C) reacting said dihydrogenphosphides with either, two equivalents of acid halides of formula (VI)

to obtain compounds of formula (III) wherein m is 2, or first with one equivalent of acid halide of formula (VI), and subsequently with one equivalent of formula (VII)

or vice versa, to obtain compounds of formula (III) wherein m is 1, and to the extent $M^3$ differs from $M^2$ further reaction with either metal salts of formula (VIII),

wherein q denotes the valence of the metal ion $M^2$, or acids of formula (IX)

wherein An is 1/p equivalent of a p-valent anion, whereby in formulae (III), (IV), (V), (VI), (VII) and (VIII), $R^2$, $R^3$, m and $M^2$ have the same meaning given above for formula (I), and LG denotes a leaving group, for example, chlorine, bromine or iodine or $C_1$-$C_8$-alkylsulfonyloxy.

Alternatively, compounds of formula (III) with m=1 are prepared, for example, by the step of contacting phosphines $H_2PR^3$, with one equivalent of acid halide of formula (VI) in the presence of two equivalents of a base or by contacting phosphides $M^3HPR^3$, with one equivalent of acid halide of formula (VI) and to the extent $M^3$ differs from $M^2$ further reaction with either metal salts of formula (VIII), whereby in formulae (III), (IV), (V), (VI), (VII) and (VIII) $R^2$, $R^3$, m and $M^2$ have the same meaning given above for formula (I) and LG denotes a leaving group, for example, chlorine, bromine or iodine or $C_1$-$C_8$-alkylsulfonyloxy.

For the avoidance of doubt, compounds of formula (III) as depicted above shall also encompass their isomers of formulae (IIIa), (IIIb) and (IIIc) which are typically present and observable in solution and solid state:

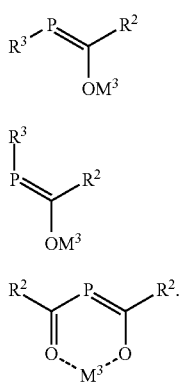

(IIIa)

(IIIb)

(IIIc)

Formula (III) as depicted above shall also encompass dimers, trimers and higher aggregated complexes as well as solvate complexes or other compounds, wherein the Metal is complexed of the compounds depicted therein, and the isomers of formulae (IIIa), (IIIb) and (IIIc) which are typically present and observable in solution and solid state.

In an embodiment of the present invention, in compounds of formulae (IVa) and (I), with $R^1$ being a substituent of formula (IIa)

n is 1 and m is 1 or 2, for example, 2 and

Z is a substituent selected from the group consisting of —CN, —(CO)$R^8$, —(CO)O$R^8$, —(CO)N($R^8$)$_2$, —(SO$_2$)$R^8$, —(PO)($R^8$)$_2$, —(PO)(O$R^8$)$_2$, —(PO)(O$R^8$)($R^8$), or 2-pyridyl $R^6$ and $R^7$ independently of each other, are hydrogen, Z or $R^8$, and $R^8$ independently of further substituents $R^8$ which may be present in the substituent of formula (IIa) is $C_1$-$C_4$-alkyl, $C_2$-$C_4$-alkenyl or $C_6$-$C_{14}$-aryl or two substituents $R^8$ irrespective of whether they are both part of a substituent Z or belong to different substituents selected from Z, $R^6$ and $R^7$ together are $C_1$-$C_4$-alkanediyl or $C_2$-$C_4$-alkenediyl, or alternatively, where two substituents —(CO)$R^8$ are present within the substituent of formulas (IIa), are together —O— or —NR$^4$—, whereby the $C_1$-$C_4$-alkyl, $C_2$-$C_4$-alkenyl, $C_1$-$C_4$-alkanediyl and $C_2$-$C_4$-alkenediyl substituents are either not, or once interrupted by non-successive functional groups selected from the group consisting of: —O—, —NR$^4$—, —CO—, —O(CO)—, (CO)O— or —O(CO)O—, and, either not, additionally or alternatively either once, twice or more than twice substituted by substituents selected from the group consisting of:

oxo, hydroxy, halogen, cyano, $C_6$-$C_{14}$-aryl, $C_1$-$C_4$-alkyl, $C_1$-$C_4$-alkoxy, $C_2$-$C_4$-alkenyl, PO(O$R^5$)$_2$, —N($R^4$)$_2$, —CO$_2$N($R^5$)$_2$, —Si(O$R^5$)$_y$($R^5$)$_{3-y}$, —OSi(O$R^5$)$_y$($R^5$)$_{3-y}$ with y=1, 2 or 3, and, for example, also —N($R^4$)$_3^+$An$^-$.

In an embodiment of the present invention, in compounds of formulae (IVa) and (I), with $R^1$ being a substituent of formula (IIa), n is 1 and m is 1 or 2, for example, 2, and Z is a substituent selected from the group consisting of —CN, —(CO)$R^8$, —(CO)O$R^8$, —(CO)N($R^8$)$_2$, —(SO$_2$)$R^8$, —(PO)($R^8$)$_2$, —(PO)(O$R^8$)$_2$, or 2-pyridyl, $R^6$ is hydrogen, $R^7$ is hydrogen, Z or $R^8$, and $R^8$ independently of further substituents $R^8$ which may be present in the substituent of formula (IIa) is $C_1$-$C_4$-alkyl, $C_2$-$C_4$-alkenyl or two substituents $R^8$ irrespective of whether they are both part of a substituent Z or belong to different substituents selected from Z, $R^6$ and $R^7$ together are $C_1$-$C_4$-alkanediyl or $C_2$-$C_4$-alkenediyl or alternatively, where two substituents —(CO)$R^8$ are present within the substituent of formulas (IIa), are together —O— or —NR$^4$—, whereby the $C_1$-$C_4$-alkyl, $C_2$-$C_4$-alkenyl, $C_1$-$C_4$-alkanediyl and $C_2$-$C_4$-alkenediyl substituents are either not, or once interrupted by non-successive functional groups selected from the group consisting of: —O—, —NR$^4$—, —CO— and, either not, additionally or alternatively once, twice or more than twice substituted by substituents selected from the group consisting of:

oxo, hydroxy, $C_1$-$C_4$-alkoxy, $C_2$-$C_4$-alkenyl, PO(O$R^5$)$_2$, —N($R^4$)$_2$, —CO$_2$N($R^5$)$_2$, —Si(O$R^5$)$_y$($R^5$)$_{3-y}$, —OSi(O$R^5$)$_y$($R^5$)$_{3-y}$ with y=1, 2 or 3, and, for example, also —N($R^4$)$_3^+$An$^-$, In an embodiment of the present invention, in compounds of formulae (IVa) and (I), with $R^1$ being a substituent of formula (IIa)

n is 1 and m is 1 or 2, for example, 2, and

Z is a substituent selected from the group consisting of —CN, —(CO)O$R^8$, —(SO$_2$)$R^8$, —(PO)($R^8$)$_2$, —(PO)(O$R^8$)$_2$, or 2-pyridyl, $R^6$ is hydrogen, $R^7$ is hydrogen, Z or Methyl, and $R^8$ independently of further substituents $R^8$ which may be present in the substituent of formula (IIa) is $C_1$-$C_4$-alkyl, $C_2$-$C_4$-alkenyl, or two substituents $R^8$ irrespective of whether they are both part of a substituent Z, or belong to different substituents selected from Z, $R^6$ and $R^7$ together are $C_1$-$C_4$-alkanediyl or $C_2$-$C_4$-alkenediyl, or alternatively, where two substituents —(CO)$R^8$ are present within the substituent of formulas (IIa), are together —O— or —NR$^4$—, whereby the $C_1$-$C_4$-alkyl, $C_2$-$C_4$-alkenyl, $C_1$-$C_4$-alkanediyl and $C_2$-$C_4$-alkenediyl substituents are either not or once interrupted by non-successive functional groups selected from the group consisting of: —O—, —NR$^4$—, and, either not, additionally, or alternatively once, twice or more than twice substituted by substituents selected from the group consisting of:

hydroxy, $C_1$-$C_4$-alkoxy, $C_2$-$C_4$-alkenyl, $PO(OR^5)_2$, —$N(R^4)_2$, —$CO_2N(R^5)_2$, —$Si(OR^5)_y(R^5)_{3-y}$, —$OSi(OR^5)_y(R^5)_{3-y}$, with y=1, 2 or 3, and, for example, also —$N(R^4)_3{}^+An^-$, In an embodiment of the present invention, the following compounds of formulae (IVa) are used:
  $C_1$-$C_8$-alkyl esters of acrylic acid or methacrylic acid whereby $C_1$-$C_8$-alkyl is unsubstituted or substituted according to the substitution pattern described above, for example, methyl-, ethyl-, n-butyl-, iso-butyl, tert.-butyl-, 2-ethylhexyl- and 2-hydroxyethyl acrylate, isobornyl acrylate, 3-(acryloyloxy) propyltrimethoxy-silane, 2-acryloxyethyltrimethylammoniumchloride,
  α-unsaturated sulfones such as phenylvinyl sulfone,
  α-unsaturated lactones such as α-methylene-γ-butyrolactone,
  α-unsaturated $C_1$-$C_8$-alkyl phosphonates compounds such as diethyl vinylphosphonate,
  aromatic compounds such as 2- and 4-vinylpyridine,
  nitriles such as acrylonitrile,
  $C_1$-$C_8$-alkyl esters of other unsaturated acids such as crotonic acid, maleic acid, fumaric acid, itaconic acid and cinnamic acid whereby $C_1$-$C_8$-alkyl is unsubstituted or substituted according to the substitution pattern described above,
  anhydrides of maleic acid and itaconic acid,
  and the respective compounds of formula (I) are those obtainable by the respective reaction of compounds of formula (IVa) with compounds of formula (III).

In an embodiment of the present invention, the following compounds of formulae (IVa) are used:
  Itaconic anhydride, maleimide, acrylonitrile, α-methylene-γ-butyrolactone, phenyl vinyl sulfone, diethyl vinylphosphonate, methylacrylate, 3-(acryloyloxy)propyltrimethoxy-silane, dimethyl itaconate, vinyl acrylate, 2-vinylpyridine, 2-acrylamido-2-hydroxymethyl-1,3-propanediol.

In an embodiment of the present invention, compounds of formulae (IVb) and (I), with $R^1$ being a substituent of formula (IIb) $R^6$ is hydrogen, $R^8$ is $C_1$-$C_8$-alkyl; and An- is a halide. An example of a compound of formula (IVb) is N,N-dimethylmethyleneiminium chloride.

In an embodiment of the present invention, compounds (IVc) and (I), with $R^1$ being a substituent of formula (IIc) $R^6$ is $C_1$-$C_8$-alkyl or $C_6$-$C_{14}$-aryl and $R^8$ is $C_1$-$C_8$-alkyl or $C_6$-$C_{14}$-aryl.

In an embodiment of the present invention, compounds of formulae (IVd) and (I), with $R^1$ being a substituent of formula (IId) $R^8$, is $C_1$-$C_8$-alkyl, $C_2$-$C_8$-alkyl or $C_6$-$C_{14}$-aryl. An example of a compound of formula (IVd) is cyclohexylisocyanate.

In an embodiment of the present invention, in compounds of formulae (IVe) and (I), with $R^1$ being a substituent of formula (IIe)
  n is 2 and m is 1 or 2, for example, 2, and
  R* is —CO— or —$SO_2$—, for example, —$SO_2$—, and
  $R^9$ independently of each other are hydrogen, $C_1$-$C_8$-alkyl, or two substituents $R^9$ irrespective of whether they are both bound to $C_{(2)}$ or not are together $C_2$-$C_8$-alkanediyl, for example, all substituents $R^9$ are hydrogen.

One specific compound of formula (IVe) is divinylsulfone.

In an embodiment of the present invention, in compounds of formulae (I), with $R^1$ being a substituent of formula (IIa) or (IIe)
  m is 1 or 2, for example, 2, and R* is a substituent of formula (VIa) or (VIb) or (VIc) or (VId) or (VIe)

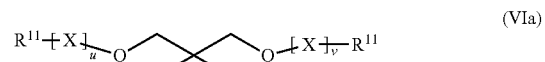

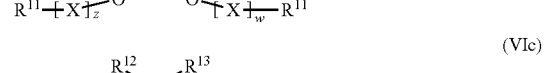

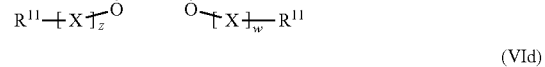

wherein,
in formula (VIa) n is 1, 2, 3 or 4,
in formula (VIb) n is 1, 2 or 3,
in formula (VIc) and VI(d) n is 1 or 2,
in formula (VIe) n is 1,
and wherein,
  n of the substituents $R^{11}$ are —$C_{(1)}H_2$—$C_{(2)}HR^{15}$—(C=O)— wherein (1) indicates the numeration of the carbon atom whereby each of the n $C_{(1)}$ carbon atoms is bound to the central phosphorous atom depicted in formula (I) and $R^{11}$ is bound to X at the carbonyl carbon and wherein $R^{15}$ is hydrogen or methyl,
  and the remainder substituents $R^{11}$, if any, are either hydrogen or $C_{(1)}H_2$=$C_{(2)}HR^{15}$—(C=O)—,
  each X is independently selected from the group consisting of
    —$OCH_2$—$CH_2$—,     —$OCH(CH_3)$—$CH_2$—,
    —$OCH_2$—$CH(CH_3)$—,  —$OCH_2$—$C(CH_3)_2$—,
    —O—$C(CH_3)_2$—$CH_2$—, and
  u, v, w and z are independently selected from 0 or an integer from 1 to 20, for example, 0 or an integer from 1 to 10, for example, zero or an integer from 1 to 5.

In an embodiment of the present invention, u, v, w and z are all 0,
  zz is selected from an integer of from 1 to 100, for example, an integer of from 2 to 100, for example, an integer of from 3 to 20,
  $R^{12}$ and $R^{13}$ are independently selected from the group consisting of hydrogen or $C_6$-$C_{14}$-aryl or $C_1$-$C_{18}$-alkyl,
  $R^{14}$ is $C_2$-$C_{18}$-alkane-diyl or $X_2$ wherein $X_2$ is independently selected from the group consisting of
    —$CHR^{16}$—$CH_2$—(O—$CHR^{16}$—$CH_2$—$)_f$—O—(CHR^{16}CH_2)$—,    —$CH_2$—$CHR^{16}$—(O—$CH_2$—$CHR^{16}$—$)_f$—O—(CHR^{16}CH_2)$—, with f being 0 or an integer of 1 to 20 and $R^{16}$ being methyl or hydrogen,
  $R^{30}$ is selected from the group consisting of hydrogen or $C_6$-$C_{14}$-aryl or $C_1$-$C_{18}$-alkyl, for example, hydrogen, methyl, ethyl, n-propyl, isopropyl, tert.-butyl and phenyl.

Compounds of formulae (VIa) to (VIe) may be obtained by reacting the compounds of formulae (VIIa) to (VIIe) with compounds of formula (III):

$$R^{17}+X+_{u}O \qquad O+X+_{v}R^{17}$$
$$R^{17}+X+_{z}O \qquad O+X+_{w}R^{17}$$
(VIIa)

$$R^{12}$$
$$\qquad O+X+_{v}R^{17}$$
$$R^{17}+X+_{z}O \qquad O+X+_{w}R^{17}$$
(VIIb)

$$R^{12} \quad R^{13}$$
$$R^{17}+X+_{z}O \qquad O+X+_{w}R^{17}$$
(VIIc)

$$R^{14}$$
$$R^{17}+X+_{z}O \qquad O+X+_{w}R^{17}$$
(VIId)

$$R^{17}+X-]_{zz}OR^{30},$$
(VIIe)

wherein, the substituents $R^{17}$ are each independently, for example, identically selected from the group consisting of hydrogen or $C_{(1)}H_2=C_{(2)}HR^{15}-(C=O)-$.

Specific compounds of formula (VIIa) are mono-, di-, tri- or tetraacrylated or -methacrylated pentaerythrol or mixtures thereof or their ethoxylated or propoxylated or mixed ethoxylated and propoxylated analogoues.

Specific compounds of formula (VIIb) are mono-, di- or tri-acrylated or -methacrylated trimethylolpropane or mono-, di- or tri-acrylated or -methacrylated glycerol or mixtures thereof or their ethoxylated or propoxylated or mixed ethoxylated and propoxylated analogoues. Further examples include 1,3-propanedioldiacrylate and 1,3-butanedioldiacrylate.

Specific compounds of formula (VIIc) are, 1,3-butanedioldiacrylate, 1,5-pentanedioldiacrylate, 1,6-hexanedioldiacrylate, glyceroldi- or -triacrylate, di- or polyacrylates of sugar alcohols such as sorbitol, mannitol, diglycerol, threitol, erythrol polyethylenglycols, epoxy(meth)acrylates, urethane(meth)acrylates, and polycarbonate(meth)acrylates.

Specific compounds of formula (VIId) are 1,2-propanedioldiacrylate, 1,4-butanedioldiacrylate, 1,5-pentanedioldiacrylate, 1,6-hexanedioldiacrylate, mono, di- or polyacrylates of sugar alcohols such as sorbitol, mannitol, diglycerol, threitol, erythrol polyethylenglycols.

Specific compounds of formula (VIIe) are acrylic or methacrylic esters of monomethyl or monoethylethers of polyethylene glycols or polypropylene glycols wherein zz is an integer of 2 to 100, for example, 3 to 20.

Compounds of formulae (VIa) to (VId) are particularly useful as multifunctional photoinitiators having highly valuable crosslinking and bonding capabilities which were not known before.

Compounds of formulae (VIa) to (VId) where at least one of u, v, z, and y is not zero and those compounds of formula (VIe) are particularly useful as photoinitiators having (in addition thereto) high efficiency as well as good emulsifying capabilities which allows to use them as photoinitiators in emulsion polymerizations with superior performance.

In an embodiment of the present invention, in compounds of formulae (I) and (III), m is 1 or 2, for example, 2, and $R^2$ is $C_6$-$C_{14}$-aryl or heterocyclyl, or is $C_1$-$C_{18}$-alkyl or $C_2$-$C_{18}$-alkenyl which is either not, once, twice or more than twice interrupted by non-successive functional groups selected from the group consisting of:

—O—, —NR$^4$—, —N$^+$(R$^4$)$_2$An$^-$-, —CO—, NR$^4$(CO)—, —NR$^4$(CO)O—, (CO)NR$^4$—, and which is not, additionally or alternatively either once, twice or more than twice substituted by substituents selected from the group consisting of:

halogen, cyano, $C_6$-$C_{14}$-aryl; heterocyclyl, $C_1$-$C_8$-alkyl, $C_1$-$C_8$-alkoxy, $C_1$-$C_8$-alkylthio, $C_2$-$C_8$-alkenyl, $C_4$-$C_{15}$-arylalkyl, —COOM, SO$_2$N(R$^3$)$_2$—, N(R$^4$)$_2$—, —N$^+$(R$^4$)$_3$An$^-$, —CO$_2$N(R$^4$)$_2$, whereby $R^4$ is independently selected from the group consisting hydrogen, $C_1$-$C_8$-alkyl, $C_6$-$C_{14}$-aryl, $C_7$-$C_{15}$-arylalkyl and heterocyclyl or N(R$^4$)$_2$ as a whole is a N-containing heterocycle or N$^+$(R$^4$)$_2$An$^-$ and N$^+$(R$^4$)$_3$An$^-$ as a whole is or contains a cationic N-containing heterocycle with a counteranion, $R^5$ is independently selected from the group consisting $C_1$-$C_8$-alkyl, $C_6$-$C_{14}$-aryl, $C_7$-$C_{15}$-arylalkyl and heterocyclyl or N(R$^5$)$_2$ as a whole is a N-containing heterocycle or N$^+$(R$^5$)$_2$An$^-$ and N$^+$(R$^5$)$_3$An$^-$ as a whole is or contains a cationic N-containing heterocycle with a counteranion, M is hydrogen, lithium, sodium, potassium, one half equivalent of calcium, zinc or iron (II), or one third equivalent of aluminium (III) or is an ammonium ion or a primary, secondary, tertiary or quarternary organic ammonium ion, and An$^-$ is 1/p equivalent of an p-valent anion.

In an embodiment of the present invention, in compounds of formulae (I) and (III), m is 2, $R^2$ is $C_6$-$C_{14}$-aryl, for example, mesityl or 2,6-dimethoxyphenyl.

In an embodiment of the present invention, in compounds of formula (I), $M^2$ is hydrogen or sodium.

The process is typically carried out by adding the compounds of formulae (IVa) to (IVf) either neat or dissolved or suspended in a solvent to a neat compound of formula (III) or a solution or suspension thereof and, where $M^2$ is hydrogen, the base. A reaction mixture is thereby formed.

The process is alternatively carried out by adding the compound of formula (III) either neat or dissolved or suspended in a solvent and, where $M^2$ is hydrogen, the base to a neat compound of formula (IVa) to (IVf) or a solution or suspension thereof. A reaction mixture is thereby formed.

The reaction time is typically in the range of from 5 min to 24 hours, for example, 30 min to 12 hours.

Suitable solvents are those which do not or virtually not react under formation of new covalent bonds with the compounds of formulae (III) and (IVa) to (IVf) employed in the reaction.

Such solvents include:

aromatic solvents such as benzene, toluene and the isomeric xylenes, ethers such as diethylether, methyl tert.butyl ether, tetrahydrofurane, dioxane, dimethoxyethane, diethoxyethan and higher glycolethers, $C_1$-$C_8$ mono-, di- or trialcohols or ether alcohols such as methanol, ethanol, n-propanol, isopropanol, glycerol, glycol, 1,4-butanediol, diethyleneglycol or triethyleneglycol, amides such as dimethylformamide, sulfones such as tetraethylensulfone, esters such as ethylacetate, and water, or mixtures of the aforementioned solvents.

It is quite surprising that the reaction can be carried out in water since this allows the process to be performed in an environmentally-friendly manner.

The amount of solvent is not critical and is only limited by commercial aspects, since they must be removed if the compounds shall finally be isolated. The amount of solvent is typically chosen so that the final product is completely soluble in the organic solvent.

To facilitate the reaction mixing energy is introduced into the reaction mixture, e.g., by standard agitators stirrers and/or by static mixing elements.

Even though not necessary, mixing can also be supported by using high force dispersion devices such as, for example, ultrasound sonotrodes or high pressure homogenizers.

The process may either be performed batchwise or continuously.

A typical reaction temperature range to carry out the process is from −30° C. to 120° C., for example, from −10 to 80° C., and for example, from 0 to 40° C.

It is evident to those skilled in the art, that where the desired reaction temperature is above the boiling point at 1013 hPa of the solvent employed, the reaction is carried out under sufficient pressure.

A typical reaction pressure range to carry out the process can, for example, be from 50 hPa to 10 MPa, for example, from 500 hPa to 1 MPa, and for example, from 800 hPa to 1.2 MPa. The reaction can, for example, be carried out under ambient pressure.

During the reaction compounds of formula (I) are formed. If $M^2$ is 1/q equivalent of an q-valent metal ion or a quarternary organic ammonium ion or a heterocyclylium cation salts of compounds of formula (I) are formed which are also covered by the present invention. In this case an acid is added after the reaction to obtain compounds of formula (I). Suitable acids are those having a pKa of 7 or less, for example, 5 or less, for example, 2 or less at 25° C. measured in water.

Examples of suitable acids include hydrogen chloride in diethylether, sulphuric acid, carboxylic acids such as formic acid and acetic acid.

If $M^2$ is hydrogen the reaction is carried out in the presence of base. Where in addition to compounds of formula (III) where $M^2$ is hydrogen further compounds of formula (III) are used where $M^2$ is not hydrogen, the latter compounds can serve as a base without the necessity to add other bases The amount of base is not critical and might be in the range of from 0.0001 to 100 mol equivalents with respect to the compounds of formula (III), for example, in the range of from 0.001 to 10 mol equivalents, for example, in the range of from 0.05 to 1 mol equivalents, for example, in the range of from 0.05 to 0.5 mol equivalents.

Suitable bases include Ammonia, primary, secondary or tertiary amines such as triethylamine, triethanolamine and DBN, N-heteroaromatic compounds such as unsubstituted or substituted pyridines or chinolines, alcoholates such as lithium-, sodium- and potassium-methoxide, -ethoxide and -tert. butoxide, amides such as lithium-diisoproylamide, hydroxides such as lithium, sodium and potassium hydroxide and carbonates such as lithium, sodium and potassium carbonate. The carbonates and hydroxides can, for example, be employed when water is used as solvent.

In an embodiment of the present invention, the bases are removed after reaction from the reaction mixture by adding an acid, for example, those acids as defined above, and removing the salts formed thereby by sedimentation and decanting, filtration or centrifugation.

The molar ratio of compounds of formula (IVa) to (IVe) to those of formula (III) depends on the integer n, i.e. the number of acylphosphino groups to be finally present in compounds of formula (I). Typically from 0.8 to 1.2 mol of compounds of formula (III) are employed per acylphosphino group to be introduced, for example, 0.9 to 1.0 mol.

Most of the compounds obtained by the reaction according to the present invention are novel. One further aspect of the present invention therefore relates to the novel compounds of formula (I) with compounds:

tert.-butyl 3-(bis(2,4,6-dimethoxybenzoyl)phosphino)propanoate, 3-(bis(2,4,6-trimethylbenzoyl)phosphino)propanitrile, and 2-(bis(2,4,6-trimethylbenzoyl)phosphino)ethyl-diethylphosphonate, being excluded since they have previously been described in WO 2006/056541.

The substitution pattern disclosed above for compounds of formula (I) also applies here.

Specific examples include:

3-((bis(2,4,6-trimethylbenzoyl)phosphino)methyl)-dihydrofuran-2,5-dione, 3-(bis(2,4,6-trimethylbenzoyl)phosphino)pyrrolidine-2,5-dione, 3-(bis(2,4,6-trimethylbenzoyl)phosphino)propanenitrile, 3-((bis(2,4,6-trimethylbenzoyl)phosphino)methyl)-dihydrofuran-2(3H)-one, di-(2-(bis(2,4,6-trimethylbenzoyl)phosphino)ethyl)-sulfone, ((bis(2,4,6-trimethylbenzoyl)phosphino)ethyl)-phenyl-sulfone, Diethyl 2-(bis(2,4,6-trimethylbenzoyl)phosphino)ethylphosphonate, methyl 3-(bis(2,4,6-trimethylbenzoyl)phosphino)propanoate, 3-(trimethoxysilyl)propyl 3-(bis(2,4,6-trimethylbenzoyl)phosphino)propanoate, dimethyl 2-((bis(2,4,6-trimethylbenzoyl)phosphino)methyl)succinate, vinyl 3-(bis(2,4,6-trimethylbenzoyl)phosphino)propanoate, N,N-methylene-(bis-(bis(2,4,6-trimethylbenzoyl)phosphino)propanamide), 2-(2-(bis(2,4,6-trimethylbenzoyl)phosphino)ethyl)-pyridine, (bis(2,4,6-trimethylbenzoyl)phosphoryl)-N-cyclohexylformamide, N-((bis(2,4,6-trimethylbenzoyl)phosphino)methyl)-N,N-dimethylamine, N-((bis(2,4,6-trimethylbenzoyl)phosphino)methyl)-N,N,N-trimethylammonium triflate, 3-(bis(2,4,6-trimethylbenzoyl)phosphino)propanoic acid 2-(2-ethoxyethoxy)ethylester, bis-(3-[2-(2-ethoxyethoxy)ethoxycarbonyl]-propyl-(2,4,6-trimethylbenzoyl)-phosphine, trimethylolpropane tris-[3-(bis(2,4,6-trimethylbenzoyl)phosphino)propanoate], trimethylolpropane monoacrylate bis-[3-(bis(2,4,6-trimethylbenzoyl)phosphino)propanoate], trimethylolpropane bisacrylate mono-[3-(bis(2,4,6-trimethylbenzoyl)phosphino)propanoate], dimethyl 2-(bis(2,4,6-trimethylbenzoyl)phosphino)fumarate, dimethyl 2-(bis(2,4,6-trimethylbenzoyl)phosphino)maleate, and 3-(bis(2,4,6-trimethylbenzoyl)phosphino)propanoyl-oxyethyltrimethylammonium chloride.

Compounds or formula (I) are particularly useful as precursor materials for compounds of formula (V)

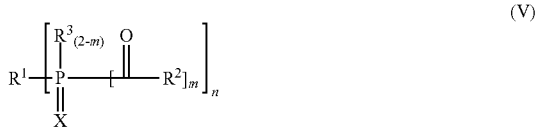

(V)

wherein, $R^1$, $R^2$, $R^3$, n and m have the same meaning as described for formula (I) above including the same example areas, and X is oxygen or sulphur, for example, oxygen.

Most of the compounds of formula (V) are also novel. An aspect of the present invention therefore relates to said compounds of formula (V) with compounds:

tert.-butyl 3-(bis(2,4,6-dimethoxybenzoyl)phosphoryl)propanoate, 3-(bis(2,4,6-trimethylbenzoyl)phosphoryl)propanitrile, and 2-(bis(2,4,6-trimethylbenzoyl)phosphoryl)ethyl-diethylphosphonate, being excluded since they were previously described in WO 2006/056541.

The example substitution pattern disclosed above for compounds of formula (I) applies analogously.

Specific examples include:

3-((bis(2,4,6-trimethylbenzoyl)phosphoryl)methyl)-dihydrofuran-2,5-dione, 2-((bis(2,4,6-trimethylbenzoyl)phosphoryl)methyl)succinic acid, 3-(bis(2,4,6-trimethylbenzoyl)phosphoryl)pyrrolidine-2,5-dione, 3-(bis(2,4,6-trimethylbenzoyl)phosphoryl)propanenitrile, 3-((bis(2,4,6-trimethylbenzoyl)phosphoryl)methyl)-dihydrofuran-2(3H)-one, di-(2-(bis(2,4,6-trimethylbenzoyl)phosphoryl)ethyl)-sulfone, ((bis(2,4,6-trimethylbenzoyl)phosphoryl)ethyl)-phenyl-sulfone, diethyl 2-(bis(2,4,6-trimethylbenzoyl)phosphoryl)ethyl-phosphonate, methyl 3-(bis(2,4,6-trimethylbenzoyl)phosphoryl)propanoate, 3-(trimethoxysilyl)propyl 3-(bis(2,4,6-trimethylbenzoyl)phosphoryl)propanoate, dimethyl 2-((bis(2,4,6-trimethylbenzoyl)phosphoryl)methyl)succinate, vinyl 3-(bis(2,4,6-trimethylbenzoyl)phosphoryl)propanoate, N,N-methylene-bis-(bis(2,4,6-trimethylbenzoyl)phosphoryl)propanamide), 2-(2-(bis(2,4,6-trimethylbenzoyl)phosphoryl)ethyl)-pyridine, 3-(bis(2,4,6-trimethylbenzoyl)phosphoryl)-N-(1,3-dihydroxy-2-(hydroxymethyl)propan-2-yl)propanamide, (bis (2,4,6-trimethylbenzoyl)phosphoryl)-N-cyclohexylformamide, methyl 3-(phenyl(2,4,6-trimethylbenzoyl)phosphoryl)propanoate, 2-(2-(phenyl-(2,4,6-trimethylbenzoyl)phosphoryl)ethyl)-pyridine, di-(2-(phenyl-(2,4,6-trimethylbenzoyl)phosphoryl)ethyl)-sulfone, 3-(bis(2,4,6-trimethylbenzoyl)phosphoryl)propanoic acid 2-(2-ethoxyethoxy) ethylester, bis-(3-[2-(2-ethoxyethoxy)ethoxycarbonyl]-propyl-(2,4,6-trimethylbenzoyl)-phosphine oxide, trimethylolpropane tris-[3-(bis(2,4,6.trimethylbenzoyl) phosphoryl) propanoate], trimethylolpropane monoacrylate bis-[3-(bis(2,4,6.trimethylbenzoyl)phosphoryl) propanoate], trimethylolpropane bisacrylate mono-[3-(bis(2,4,6.trimethylbenzoyl)-phosphoryl) propanoate], dimethyl 2-(bis(2,4,6-trimethylbenzoyl)phosphino)fumarate, dimethyl 2-(bis(2,4,6-trimethylbenzoyl)phosphino) maleate, and 3-(bis(2,4,6-trimethylbenzoyl)phosphoryl)propanoyl-oxyethyltrimethylammonium chloride.

Compounds of formula (V) may be obtained by reaction of compounds of formula (I) with an oxidizing agent to obtain compounds of formula (V), where X is oxygen or a sulfidizing agent to obtain compounds of formula (V), where X is sulphur in a manner well known to those skilled in the art and as e.g., described in WO 2006/056541.

Suitable oxidizing agents are: hydrogen peroxide, which can, for example, be employed as aqueous solution, e.g., with 30 wt.-%, organic peroxides such as tert-butylhydroperoxide; oxygen e.g., in the form of air, or sodium hypochlorite.

Suitable sulfidizing agents are: elemental sulphur or organic polysulfides.

In an embodiment of the present invention, the oxidation or suldidation is carried out in the same reaction media as the process for the preparation of compounds of formula (I), i.e., as a one-pot-reaction.

An advantage of the process according to the present invention is that it allows the efficient and high-yielding synthesis of compounds of formulae (I) and (V) with a mild, variety of functional groups which are not easily available via known routes.

Compounds of formula (V) are particularly useful as photoinitiators. An aspect of the present invention therefore relates to a photoinitiated polymerization process, in particular, for the polymerization of polymerizable monomers wherein compounds of formula (V) are employed.

Such processes are particularly useful for the preparation of polymer nanoparticles, coatings, adhesives, inks and painting materials. The present invention therefore further relates to polymer nanoparticles, coatings, adhesives, inks and painting materials obtainable by such process.

The present invention is further illustrated by the examples without being limited thereby.

EXAMPLES

I Preparation of Precursor Materials

1) Preparation of Sodium bis(mesitoyl)phosphide

In a 100 mL thick-walled Schlenk flask equipped with a teflon screw cap, sodium (1.73 g, 0.075 mmol, 3 eq.) and red phosphorus (0.78 g, 0.025 mmol, 1 eq.) were put together under inert conditions. A glass covered magnetic stirrer was added and 20 mL of ammonia were condensed into the flask, by cooling with dry ice/acetone to −78° C. Subsequently, dimethoxyethane (dme) (20 mL) was added and the flask was closed and warmed up to room temperature. After 90 min. stirring at room temperature, a change in color from blue to dark yellow was observed and after another 30 min., the color became intensively yellow. The pressure in the reaction vessel was 7 to 8 bar. The reaction mixture was cooled down to −40° C. The Schlenk flask, which had now a pressure of 1 bar, was opened and tert-butanol (3.71 g, 0.05 mol, 2 eq.) was added. The reaction mixture was warmed up to room temperature over a period of two hours. Finally, the solvent was completely removed in vacuo at room temperature. The remaining oil was dissolved in dme (40 mL). Mesitoyl chloride (9.15 g, 0.05 mol, 2 eq.) was added dropwise.

i): Isolation of the product under dry conditions: The reaction mixture was stirred for one hour at room temperature, the precipitate of sodium chloride was removed by filtration, and the solvent was evaporated in vacuo. The pure microcrystalline product can be obtained by dissolving the sodium bis(mesitoyl)phosphide in dme and precipitation with n-hexane (Yield: 5.89 g, 67.7%).

ii). Working up with degassed water: The reaction mixture was mixed with 100 mL degassed, distilled water. After stirring, the solution until the sodium chloride was completely dissolved, the reaction mixture was extracted three times with 50 mL of toluene. After removing the toluene in vacuo, the pure product remains. It can contain small amounts of water, which can be completely removed by azeotropic distillation with toluene. The product is dissolved in toluene and the solvent is removed in vacuo afterwards again. This procedure must be repeated two or three times. The yield is the same as for procedure a).

m.p.: 208° C. (Decomposition).
$^{31}$P NMR (101.25 MHz): δ=84.1 ppm (br.).

2) Preparation of bis(mesitoyl)phosphane (HP(COMes)$_2$)

The phosphane was obtained by adding an equimolar amount of hydrochloric acid in ether (2 M) to the compound obtained according to Example 1, filtering off the resulting sodium chloride, and evaporating the solvent in vacuo.

3) Preparation of sodium-mesitoylphenylphosphide

The phosphane PhPH$_2$ was prepared according to the procedure described by Grutzmacher et al. CHIMIA 2008, 62, No. 1/2. A solution of PhPH$_2$ (0.38 mL, 3.46 mmol) and NaO$^t$Bu (0.67 g, 6.92 mmol, 2 eq.) in toluene (10 mL) was prepared in a 50 mL Schlenk flask under an argon atmosphere. Subsequently, mesitoyl chloride (0.58 mL, 3.46 mmol, 1 eq.) was added dropwise to the solution at 0° C. The reaction mixture was allowed to warm to room temperature and stirred for 2 h, the precipitate of sodium chloride was removed by filtration and the solvent was removed in vacuo to yield a pale yellow solid (0.79 g, 2.84 mmol, 82%).

$^{31}$P{$^1$H} NMR (101.3 MHz, C$_6$D$_6$, 298 K): δ=49.8 ((E)-isomer), 83.1 ((Z)-isomer) ppm.

II Preparation of Acylphosphanes and Their Oxides

General Method for the Preparation of Acylphosphanes Starting from Phosphines and Phosphides A solution of the phosphane or phosphide and optionally triethylamine in either dimethoxyethane (dme) or tetrahydrofurane (thf) was prepared in a 50 mL Schlenk flask under an inert atmosphere of argon (first solution). Subsequently, a solution of a compound selected from those of formulae (IVa) to (IVe) in dme or thf or the neat compound (hereinafter collectively referred to as second solution) was slowly added. After stirring for twelve hours at room temperature, a 2M solution of hydrochloric acid in diethylether was added in an equimolar amount to neutralize the triethylamine. The reaction mixture was stirred for another hour at room temperature, before the solvent was removed under reduced pressure. The solid residue was dissolved in toluene and the insoluble precipitate of triethylamine hydrochloride was separated by filtration. The solution volume was reduced in vacuo to half of its volume and layered with half of the remaining volume of hexane. The obtained crystalline solid was collected and dried under high vacuum for twelve hours.

General Method for the Preparation of Acylphosphane Oxides

The oxidant was added to a solution of the acylphosphane in toluene and the reaction mixture vigorously stirred at room temperature for twelve hours under an inert atmosphere (argon) and exclusion of light in a 50 mL Schlenk flask. The solvent was thereafter removed under reduced pressure. The resulting product was recrystallized from a polar solvent layered with a non polar solvent and storage at −15° under exclusion of light. The precipitate was collected by filtration and dried under vacuum for twelve hours.

4a) 3-((bis(2,4,6-trimethylbenzoyl)phosphino) methyl)-dihydrofuran-2,5-dione

First solution: HP(COMes)$_2$ (3 g, 9.19 mmol) and triethylamine (0.92 mmol) in dme (20 mL)
Second solution: itaconic anhydride (1.03 g, 9.19 mmol) in dme (10 mL)
Amount of toluene: 40 Ml
Yield: 3.87 g, 96% th.
$^{31}$P{$^1$H} NMR (121.5 MHz, C$_6$D$_6$, 298 K): δ=48.7 ppm 4b) 3-((bis(2,4,6-trimethylbenzoyl)phosphoryl) methyl)-dihydrofuran-2,5-dione Acylphosphane: 1.019 g (2.32 mmol) of compound obtained according to Example 4a
Amount of toluene: 15 ml
Oxidant: tert-butyl hydroperoxide (0.465 mL, 1.1 eq., 2.56 mmol, 5.5M in decane)
Recrystallization: from 7 mL toluene layered with hexane (2 mL)
Yield: 0.85 g, 81% th.
$^{31}$P{$^1$H} NMR (81 MHz, C$_6$D$_6$, 298 K): δ=22.5 ppm 4c) 2-((bis(2,4,6-trimethylbenzoyl)phosphoryl) methyl)succinic acid Acylphosphane: 1.58 g (3.60 mmol) of compound obtained according to Example 4a
Amount of toluene: 20 ml
Oxidant: aqueous hydrogen peroxide (0.82 mL, 2.2 eq., 7.93 mmol, 30%)
Recrystallization: from 35 mL diethyl ether layered with hexane (2 mL)
Yield: 1.53 g, 90% th.
$^{31}$P{$^1$H} NMR (121.5 MHz, C$_6$D$_6$, 298 K): δ=24.0 ppm 5a) 3-(bis(2,4,6-trimethylbenzoyl)phosphino)pyrrolidine-2,5-dione First solution: HP(COMes)$_2$ (0.5 g, 1.53 mmol) and triethylamine (0.15 mmol) in dme (3 mL)
Second solution: maleimide (149 mg, 1.53 mmol) in dme (2 mL)
Amount of toluene: 20 mL
Yield: 0.63 g, 97% th.
$^{31}$P{$^1$H} NMR (121.5 MHz, d8-thf, 298 K): δ=71.7 ppm 5b) 3-(bis(2,4,6-trimethylbenzoyl)phosphoryl)pyrrolidine-2,5-dione Acylphosphane: 500 mg (1.18 mmol) of compound obtained according to Example 5a
Amount of toluene: 10 ml
Oxidant: tert-butyl hydroperoxide (0.24 mL, 1.1 eq., 1.30 mmol, 5.5M in decane)
Recrystallization: none, but washing with hexane (3×7 mL)
Yield: 0.475 g, 92% th.
$^{31}$P{$^1$H} NMR (202.5 MHz, d8-thf, 298 K): δ=25.2 ppm 6a) 3-(bis(2,4,6-trimethylbenzoyl)phosphino)propanenitrile First solution: HP(COMes)$_2$ (0.5 g, 1.53 mmol) and triethylamine (0.15 mmol) in dme (5 mL)

Second solution: neat acrylonitrile (0.1 mL, 1.53 mmol)
Amount of toluene: 7 mL
Yield: 0.57 g, 99% th.
$^{31}$P NMR (162 MHz, d8-thf, 298 K): δ=49.9 ppm (t, $^2J_{PH}$=11.91 Hz)

6b) 3-(bis(2,4,6-trimethylbenzoyl)phosphoryl)propanenitrile

Acylphosphane: 418 mg (1.10 mmol) of compound obtained according to Example 6a
Amount of toluene: 5 ml
Oxidant: aqueous hydrogen peroxide (0.13 mL, 1.1 eq., 1.21 mmol, 30%)
Recrystallization: from 10 mL toluene layered with hexane (5 mL)
Yield: 0.37 g, 85% th.
$^{31}$P{$^1$H} NMR (202.5 MHz, C$_6$D$_6$, 298 K): δ=23.3 ppm 7a) 3-((bis(2,4,6-trimethylbenzoyl)phosphino)methyl)-dihydrofuran-2(3H)-one First solution: HP(COMes)$_2$ (3 g, 9.19 mmol) and triethylamine (0.92 mmol) in dme (30 mL)
Second solution: neat α-methylene-γ-butyrolactone (0.805 mL, 9.19 mmol)
Amount of toluene: 40 mL
Yield: 3.71 g, 95% th.
$^{31}$P{$^1$H} NMR (121.5 MHz, d8-thf, 298 K): δ=49.1 ppm 7b) 3-((bis(2,4,6-trimethylbenzoyl)phosphoryl)methyl)-dihydrofuran-2(3H)-one Acylphosphane: 1.118 g (2.63 mmol) of compound obtained according to Example 7a
Amount of toluene: 10 ml
Oxidant: tert-butyl hydroperoxide (0.53 mL, 1.1 eq., 2.90 mmol, 5.5M in decane)
Recrystallization: from 4 mL toluene layered with hexane (3 mL)
Yield: 0.95 g, 82% th.
$^{31}$P{$^1$H} NMR (202.5 MHz, C$_6$D$_6$, 298 K): δ=25.6 ppm 8a) di-(2-(bis(2,4,6-trimethylbenzoyl)phosphino)ethyl)-sulfone First solution: HP(COMes)$_2$ (1.455 g, 4.46 mmol) and triethylamine (0.45 mmol) in dme (15 mL)
Second solution: neat divinylsulfone (0.223 mL, 2.23 mmol)
Amount of toluene: 40 mL
Yield: 3.4 g, 99% th.
$^{31}$P{$^1$H} NMR (121.5 MHz, d8-thf, 298 K): δ=53.3 ppm 8b) di-(2-(bis(2,4,6-trimethylbenzoyl)phosphoryl)ethyl)-sulfone Acylphosphane: 1.257 g (1.63 mmol) of compound obtained according to Example 8a
Amount of toluene: 15 ml
Oxidant: aqueous hydrogen peroxide (0.37 mL, 2.2 eq., 3.59 mmol, 30%)
Recrystallization: none, but washing with hexane (3×7 mL)
Yield: 1.25 g, 96% th.
$^{31}$P{$^1$H} NMR (162 MHz, C$_6$D$_6$, 298 K): δ=23.0 ppm 9a) ((bis(2,4,6-trimethylbenzoyl)phosphino)ethyl)-phenyl-sulfone First solution: HP(COMes)$_2$ (0.5 g, 1.53 mmol) and triethylamine (0.15 mmol) in dme (3 mL)
Second solution: phenyl vinyl sulfone (258 mg, 1.53 mmol) in dme (2 mL)
Amount of toluene: 20 mL
Yield: 0.71 g, 94% th.
$^{31}$P{$^1$H} NMR (121.5 MHz, d8-thf, 298 K): δ=50.0 ppm 9b) ((bis(2,4,6-trimethylbenzoyl)phosphoryl)ethyl)-phenyl-sulfone Acylphosphane: 0.31 g (0.63 mmol) of compound obtained according to Example 9a
Amount of toluene: 5 ml
Oxidant: aqueous hydrogen peroxide (0.071 mL, 2.2 eq., 0.69 mmol, 30%)
Recrystallization: none, but washing with hexane (3×5 mL)
Yield: 0.29 g, 90% th.
$^{31}$P{$^1$H} NMR (202.5 MHz, C$_6$D$_6$, 298 K): δ=22.9 ppm 10a) Diethyl 2-(bis(2,4,6-trimethylbenzoyl)phosphino)ethylphosphonate First solution: HP(COMes)$_2$ (1.03 g, 3.16 mmol) and triethylamine (0.32 mmol) in dme (10 mL)
Second solution: neat diethyl vinylphosphonate (0.485 mL, 3.16 mmol)
Amount of toluene: 40 mL
Yield: 1.38 g, 89% th., yellow oil
$^{31}$P{$^1$H} NMR (121.5 MHz, d8-thf, 298 K): δ=30.6 ppm (d, $J_{PP}$=55.35 Hz), 57.05 ppm (d, $J_{PP}$=55.35 Hz)

10b) Diethyl 2-(bis(2,4,6-trimethylbenzoyl)phosphoryl)ethylphosphonate

Acylphosphane: 0.89 g (1.81 mmol) of compound obtained according to Example 10a
Amount of toluene: 10 ml
Oxidant: aqueous hydrogen peroxide (0.21 mL, 2.2 eq., 2.00 mmol, 30%)
Recrystallization: none, but washing with hexane (3×7 mL)
Yield: 90% th.
$^{31}$P{$^1$H} NMR (80 MHz, toluene, 298 K): δ=24.44 ppm (d, $J_{PP}$=57.6 Hz), 29.18 ppm (d, $J_{PP}$=57.6 Hz)

11a) methyl 3-(bis(2,4,6-trimethylbenzoyl)phosphino)propanoate

First solution: HP(COMes)$_2$ (514 mg, 1.57 mmol) and triethylamine (0.16 mmol) in dme (5 mL)
Second solution: neat methylacrylate (0.142 mL, 1.57 mmol)
Note: Reaction was carried out at 40° C. for twelve hours
Amount of toluene: 6 mL
Yield: 0.63 g, 98% th.
$^{31}$P{$^1$H} NMR (121.5 MHz, d8-thf, 298 K): δ=50.5 ppm 11b) methyl 3-(bis(2,4,6-trimethylbenzoyl)phosphoryl)propanoate Acylphosphane: 0.33 g (0.79 mmol) of compound obtained according to Example 11a Amount of toluene: 5 ml
Oxidant: tert-butyl hydroperoxide (0.16 mL, 1.1 eq., 0.87 mmol, 5.5M in decane)
Recrystallization: from 7 mL toluene layered with hexane (2 mL)
Yield: 0.32 g, 95% th., yellow oil after additional, final washing with 3×5 mL hexane and drying
$^{31}P\{^1H\}$ NMR (202.5 MHz, $C_6D_6$, 298 K): δ=26.5 ppm

12a) 3-(trimethoxysilyl)propyl 3-(bis(2,4,6-trimethylbenzoyl)phosphino)propanoate First solution: HP(COMes)$_2$ (3 g, 9.19 mmol) and triethylamine (0.92 mmol) in dme (30 mL)
Second solution: neat 3-(acryloyloxy)propyltrimethoxysilane (2.032 mL, 9.19 mmol)
Note: Reaction was carried out at 60° C. for twelve hours
Amount of toluene: 6 mL
Yield: 4.79 g, 93% th., yellow oil after additional, final washing with 3×7 mL hexane and drying
$^{31}P$ NMR (121.5 MHz, d8-thf, 298 K): δ=52.1 ppm (t, $^2J_{PH}$=11.48 Hz)

12b) 3-(trimethoxysilyl)propyl 3-(bis(2,4,6-trimethylbenzoyl)phosphoryl)propanoate Acylphosphane: 2.67 g (4.76 mmol) of compound obtained according to Example 12a
Amount of toluene: 20 ml
Oxidant: aqueous hydrogen peroxide (0.54 mL, 2.2 eq., 5.24 mmol, 30%)
Recrystallization: none, but washing with hexane (3×8 mL)
Yield: 87% th.
$^{31}P\{^1H\}$ NMR (121.5 MHz, CDCl$_3$, 298 K): δ=25.8 ppm

13a) dimethyl 2-((bis(2,4,6-trimethylbenzoyl)phosphino)methyl)succinate

First solution: HP(COMes)$_2$ (3 g, 9.19 mmol) and triethylamine (0.92 mmol) in dme (20 mL)
Second solution: dimethyl itaconate (1.454 g, 9.19 mmol) in dme (10 mL)
Note: Reaction was carried out at 60° C. for twelve hours
Amount of toluene: 40 mL
Yield: 4.19 g, 94% th., yellow oil after additional, final washing with 3×7 mL hexane and drying
$^{31}P\{^1H\}$ NMR (162 MHz, d8-thf, 298 K): δ=49.4 ppm

13b) dimethyl 2-((bis(2,4,6-trimethylbenzoyl)phosphoryl)methyl)succinate

Acylphosphane: 3.72 g (0.77 mmol) of compound obtained according to Example 13a
Amount of toluene: 25 ml
Oxidant: aqueous hydrogen peroxide (0.87 mL, 2.2 eq., 0.85 mmol, 30%)
Recrystallization: none, but washing with hexane (3×7 mL)
Yield: 97% th.
$^{31}P\{^1H\}$ NMR (121.5 MHz, CDCl$_3$, 298 K): δ=25.5 ppm

14a) Vinyl 3-(bis(2,4,6-trimethylbenzoyl)phosphino)propanoate

First solution: HP(COMes)$_2$ (2 g, 6.13 mmol) and triethylamine (0.61 mmol) in dme (20 mL)
Second solution: neat vinyl acrylate (0.64 mL, 6.13 mmol)
Amount of toluene: 30 mL
Yield: 2.55 g, 98% th.
$^{31}P\{^1H\}$ NMR (121.5 MHz, $C_6D_6$, 298 K): δ=51.9 ppm

14b) Vinyl 3-(bis(2,4,6-trimethylbenzoyl)phosphoryl)propanoate

Acylphosphane: 3.72 g (0.77 mmol) of compound obtained according to Example 13a
Amount of toluene: 25 ml
Oxidant: oxygen dried over phosphorous pentoxide was slowly passed through the stirred solution
Recrystallization: from toluene (3 mL) layered with hexane (1 mL)
Yield: 88% th.
$^{31}P\{^1H\}$ NMR (121.5 MHz, CDCl$_3$, 298 K): δ=24.8 ppm

15a) N,N-methylene-(bis-(bis(2,4,6-trimethylbenzoyl)phosphino)propanamide)

First solution: HP(COMes)$_2$ (2.87 g, 8.78 mmol) and triethylamine (0.88 mmol) in dme (30 mL)
Second solution: neat N,N-methylene-bis-acrylamide (0.690 g, 0.5 eq., 4.39 mmol)
Note: Reaction was carried out at 50° C. for twelve hours
Amount of toluene: 60 mL
Yield: 3.484 g, 99% th., yellow solid after additional, final washing with 3×8 mL hexane and drying
$^{31}P\{^1H\}$ NMR (121.5 MHz, d8-thf, 298 K): δ=50.5 ppm, 50.7 ppm

15b) N,N-methylene-bis-(bis(2,4,6-trimethylbenzoyl)phosphoryl)propanamide)

Acylphosphane: 2.98 g (3.70 mmol) of compound obtained according to Example 15a
Amount of toluene: 15 ml
Oxidant: aqueous hydrogen peroxide (0.84 mL, 2.2 eq., 8.14 mmol, 30%)
Recrystallization: none, but washing with hexane (3×10 mL)
Yield: 2.55 g, 82% th.
$^{31}P\{^1H\}$ NMR (202.5 MHz, CDCl$_3$, 298 K): δ=26.8 ppm

16a) 2-(2-(bis(2,4,6-trimethylbenzoyl)phosphino)ethyl)-pyridine

First solution: HP(COMes)$_2$ (3.15 g, 9.64 mmol) in dme (30 mL)
Note: Triethylamine was not added since vinylpyridine itself serves as a base
Second solution: neat 2-vinylpyridine (1.04 mL, 9.64 mmol)
Note: Reaction was carried out at 50° C. for twelve hours
Amount of toluene: 60 mL
Yield: 3.83 g, 92% th., yellow solid after additional, final washing with 3×5 mL hexane and drying
$^{31}P\{^1H\}$ NMR (202.5 MHz, dme, 298 K): δ=52.44 ppm

16b) 2-(2-(bis(2,4,6-trimethylbenzoyl)phosphoryl)ethyl)-pyridine

A 50 mL Schlenk flask was charged with HP(COMes)$_2$ (0.76 g, 2.33 mmol), which was suspended in H$_2$O (10 mL) under an argon atmosphere. Subsequently, neat 2-vinylpyridine (0.25 mL, 1 eq., 2.33 mmol) was added to the solution. The reaction mixture was allowed to stir at room temperature for 12 h. The formation of the addition product 2-(2-(bis(2,4,6-trimethylbenzoyl)phosphino)ethyl)-pyridine was confirmed by $^{31}$P-NMR spectroscopy ($\delta$=50.1 ppm). The solution was adjusted to a pH-value of 7 by adding NH$_4$Cl (76 mg, 0.61 eq., 1.42 mmol). Furthermore, aqueous H$_2$O$_2$ was added to the solution. After a reaction time of 12 h at room temperature, the reaction mixture was treated extracted with dichloromethane (2×5 mL). The organic phases were combined, dried over NaSO$_4$ and the solvent was removed in vacuo to yield a yellow solid (0.87 g, 1.98 mmol, 85%).

$^{31}$P{$^1$H} NMR (101.3 MHz, D$_2$O, 298 K): $\delta$=24.4 ppm.

16c) 2-(2-(bis(2,4,6-trimethylbenzoyl)phosphoryl)ethyl)-pyridine

Acylphosphane: 339 mg (0.79 mmol) of compound obtained according to Example 16a
Amount of toluene: none, solvent employed instead: dme (5 ml)
Oxidant: tert-butyl hydroperoxide (0.16 mL, 1.1 eq., 0.86 mmol, 5.5M in decane)
Recrystallization: none, but washed with hexane (3×5 mL)
Yield: 0.34 g, 97% th.
$^{31}$P{$^1$H} NMR (101.3 MHz, C$_6$D$_6$, 298 K): $\delta$=27.1 ppm 17) 3-(bis(2,4,6-trimethylbenzoyl)phosphoryl)-N-(1,3-dihydroxy-2-(hydroxymethyl)propan-2-yl)propanamide First solution: HP(COMes)$_2$ (500 mg, 1.53 mmol) and triethylamine (0.15 mmol) in dme (5 mL)
Second solution: neat 2-acrylamido-2-hydroxymethyl-1,3-propanediol (268 mg, 1.53 mmol)
Note: Reaction was carried out at 50° C. for twentyfour hours
Amount of toluene: 15 mL
Yield: not determined, toluene solution was directly employed for oxidation
Oxidant: aqueous hydrogen peroxide (0.17 mL, 1.1 eq., 1.68 mmol, 30%)
Recrystallization: none, but washed with hexane (3×3 mL)
Yield: 0.68 g, 86% th.
$^{31}$P{$^1$H} NMR (121.5 MHz, CDCl$_3$, 298 K): $\delta$=26.1 and 25.9 ppm 18) (bis(2,4,6-trimethylbenzoyl)phosphoryl)-N-cyclohexylformamide First solution: HP(COMes)$_2$ (1.098 g, 3.36 mmol) and triethylamine (0.17 mmol) in dme (8 mL)
Second solution: neat degassed cyclohexyl isocyanate (0.43 mL, 3.36 mmol)
Note: Reaction was carried out at room temperature for two hours
Amount of toluene: 10 mL
Yield: not determined, toluene solution was directly employed for oxidation
Oxidant: tert-butyl hydroperoxide (0.35 mL, 1.1 eq., 3.6 mmol, 5.5M in decane)
Recrystallization: none
Yield: 1.43 g, 91% th.
$^{31}$P{$^1$H} NMR (202.5 MHz, d8-thf, 298 K): $\delta$=0.1 ppm 19a) N-((bis(2,4,6-trimethylbenzoyl)phosphino)methyl)-N,N-dimethylamine First solution: NaP(COMes)$_2$ (434 mg, 1.12 mmol) in thf (5 mL)
Second solution: N,N-dimethylmethyleneiminium chloride (105 mg, 1.12 mmol) in thf (1 mL, suspension)
Amount of toluene: 20 mL, Sodium chloride was separated by filtration
Yield: 372 mg, 87% th., yellow solid after additional, final washing with 3×1 mL hexane and drying
$^{31}$P{$^1$H} NMR (162 MHz, thf, 298 K): $\delta$=39.6 ppm 19b) N-((bis(2,4,6-trimethylbenzoyl)phosphino)methyl)-N,N,N-trimethylammonium triflate A 20 mL Schlenk flask was charged with the phosphine obtained according to Example 19a) (151 mg, 0.39 mmol), which was dissolved in thf (4 mL). Subsequently, methyl triflate (45.3 µL, 0.39 mmol) in thf (5 mL) was added dropwise to the stirred solution. After a reaction time of 2 h at rt, the solvent was removed under reduced pressure. The solid residue was dissolved in an ethanol (5 mL) acetonitrile (2 mL) mixture. Subsequently, oxygen was slowly passed through the stirred solution at room temperature for 1 h. The solvent was removed in vacuo and the pale yellow solid obtained was recrystallised from dichloromethane. The product was dried under high vacuum for twelve hours to yield 196 mg (0.35 mmol, 89% th.).
$^{31}$P{$^1$H} NMR (101.3 MHz, CDCl$_3$, 298 K): $\delta$=10.3 ppm 20) methyl 3-(phenyl(2,4,6-trimethylbenzoyl)phosphoryl)propanoate A solution of NaPPh(COMes) (30 mg, 0.11 mmol) prepared according to Example 3 in dme (0.5 mL) was prepared in an NMR-tube. Subsequently, a diethyl ether solution of hydrochloric acid (65 µL, 0.13 mmol, 1.2 eq., 2M) was added. After mixing, the solution was concentrated under reduced pressure. The white solid residue of HPPh(COMes) was dissolved in dme (0.5 mL). A $^{31}$P-NMR spectrum was recorded to observe the chemical shifts for the enol and keto form of HPPh(COMes) $\delta$=49.90 ppm (s) and $\delta$=−20.11 ppm (d, $J_{PH}$=235 Hz) respectively.

Methyl acrylate (19.5 µL, 0.22 mmol, 2 eq.) and triethylamine (5 µL, 0.04 mmol, 33 mol-%) were added to the solution, which was then warmed to 60° C. for twelve hours. Product formation was confirmed by $^{31}$P-NMR spectroscopy $\delta$=11.12 ppm (101.3 MHz, dme, 298 K).

Finally, aqueous hydrogen peroxide (17 µL, 0.16 mmol, 1.5 eq., 30%) was added to the solution and mixed for one hour. The desired product was obtained, which could be confirmed by $^{31}$P-NMR spectroscopy.
$^{31}$P{$^1$H} NMR (202.5 MHz, dme, 298 K): $\delta$=27.9 ppm 21) 2-(2-(phenyl-(2,4,6-trimethylbenzoyl)phosphoryl)ethyl)-pyridine A solution of NaPPh(COMes) (30 mg, 0.11 mmol) prepared according to Example 3 in dme (0.5 mL) was prepared in an NMR-tube. Subsequently, a diethyl ether solution of hydrochloric acid (65 µL, 0.13 mmol, 1.2 eq., 2M) was added. After mixing, the solution was concentrated under reduced pressure. The white solid residue of HPPh(COMes) was dissolved in dme (0.5 mL). A $^{31}$P-NMR spectrum was recorded to observe the chemical shifts for the enol and keto form of HPPh(COMes) δ=49.90 ppm (s) and δ=−20.11 ppm (d, $J_{PH}$=235 Hz) respectively.

2-Vinylpyridine (23 μL, 0.22 mmol, 2 eq.) and was added to the solution, which was then warmed to 60° C. for twelve hours. Product formation was confirmed by $^{31}$P-NMR spectroscopy δ=14.65 ppm (202.5 MHz, dme, 298 K).

Finally, aqueous hydrogen peroxide (17 μL, 0.16 mmol, 1.5 eq., 30%) was added to the solution and mixed for one hour. The desired product was obtained, which could be confirmed by $^{31}$P-NMR spectroscopy.

$^{31}$P{$^{1}$H} NMR (202.5 MHz, dme, 298 K): δ=29.4 ppm.

22) di-(2-(phenyl-(2,4,6-trimethylbenzoyl)phosphoryl)ethyl)-sulfone

A solution of NaPPh(COMes) (30 mg, 0.11 mmol) prepared according to Example 3) in dme (0.5 mL) was prepared in an NMR-tube. Subsequently, a diethyl ether solution of hydrochloric acid (65 μL, 0.13 mmol, 1.2 eq., 2M) was added. After mixing, the solution was concentrated under reduced pressure. The white solid residue of HPPh (COMes) was dissolved in dme (0.5 mL). A $^{31}$P-NMR spectrum was recorded to observe the chemical shifts for the enol and keto form of HPPh(COMes) δ=49.90 ppm (s) and δ=−20.11 ppm (d, $J_{PH}$=235 Hz) respectively.

Divinyl sulfone (5.4 μL, 0.06 mmol, 0.5 eq.) and was added to the solution, which was then warmed to 60° C. for twelve hours. Product formation was confirmed by $^{31}$P-NMR spectroscopy δ=11.66 ppm (202.5 MHz, dme, 298 K).

Finally, aqueous hydrogen peroxide (17 μL, 0.16 mmol, 1.5 eq., 30%) was added to the solution and mixed for one hour. The desired product was obtained, which could be confirmed by $^{31}$P-NMR spectroscopy.

$^{31}$P NMR (202.5 MHz, dme, 298 K): δ=26.4 ppm.

23) 3-(bis(2,4,6-trimethylbenzoyl)phosphoryl)propanoic acid 2-(2-ethoxyethoxy)ethylester Bis(mesitoyl)phosphane (HP(COMes)$_2$, 3.916 g, 12 mmol) was dissolved in dme (40 ml) under argon and 2-(2-ethoxyethoxy) ethyl acrylate (2.259 g, 12 mmol, 1 eq.) and NEt$_3$ (0.17 ml, 1.2 mmol, 10%) was added. The reaction mixture was stirred at room temperature for 12 h before HCl was added (2M in diethyl ether, 0.6 mL, 1.2 mmol, 0.1 eq.) dropwise at 0° C. The mixture was stirred for 30 min. and then dme was removed under reduced pressure. The residue was dissolved in toluene (20 mL) and the precipitated triethylamine hydrochloride was removed by filtration. Subsequently, aqueous hydrogen peroxide (30%, 0.8 mL, 2.2 eq.) was added under exclusion of light over a period of 15 minutes at 0° C. Subsequently, the reaction mixture was stirred for 6 h. The resulting yellow solution was concentrated and dissolved in 20 mL THF and dried over Na$_2$SO$_4$. After filtration, the solvent was removed under vacuum for 12 h to yield 5.437 g (10.25 mmol, 85.4%) of a yellow oil.

$^{31}$P{$^{1}$H} NMR (121.5 MHz, CDCl$_3$) δ[ppm]=25.09.

24) Bis-(3-[2-(2-ethoxyethoxy)ethoxycarbonyl]-propyl-(2,4,6-trimethylbenzoyl)-phosphine oxide Red phosphorous (P$_4$, 0.248 g, 2 mmol) and naphthalene (0.104 g, 0.8 mmol, 0.1 eq.) were suspended in 10 ml dme. Freshly cut sodium pieces (Na, 0.552 g, 24 mmol, 3 eq.) were subsequently added to the suspension. The mixture was stirred for 12 hours, $^t$BuOH (1.61 ml, 16 mmol, 2 eq.) in 5 ml dme was then added dropwise to the mixture at 0° C. The resulting black suspension was stirred for an additional 2 hours. Subsequently, mesityl(ethylcarboxylate) (1.78 mL, 8.8 mmol, 1.1 eq.) was added and reacted at 60° C. for 16 h to give Na[HP—CO(Mes)]. To this yellow suspension, HCl (2M in diethyl ether, 12 mL, 24 mmol, 3 eq.) was added dropwise at 0° C. and the reaction mixture was stirred for 30 min. Subsequently, the solvent and all volatiles were removed under reduced pressure. The residue was again dissolved in dme (10 ml) and 2-(2-ethoxyethoxy) ethyl acrylate (3.0 ml, 16 mmol, 2 eq.) and 1,5-diazabicyclo-[4,3,0]-non-5-ene (DBN, 0.1 ml, 0.8 mmol, 10%) were added at 0° C. The mixture was warmed to room temperature and stirred for 1 h. Then HCl (2M in Diethyl ether, 0.4 mL, 0.8 mmol, 0.1 eq.) was added dropwise at 0° C. and the mixture stirred for 30 min before dme and all volatiles were removed under reduced pressure. The residue was dissolved in toluene (25 mL) and the precipitated salts were removed by filtration. Subsequently, aqueous hydrogen peroxide (30%, 1.9 mL, 2.3 eq.) was added under exclusion of light over a period of 15 minutes at 0° C. and the mixture stirred for 1 h. The resulting yellowish solution was concentrated and dissolved in 50 mL dichloromethane and dried over Mg$_2$SO$_4$. After filtration the solvent was removed and the residue dried for 12 h under vacuum to yield 3.679 g (6.43 mmol, 80.3%) of a slightly yellow oil.

$^{31}$P{$^{1}$H} NMR (121.5 MHz, CDCl$_3$) δ[ppm]=38.5.

25a) trimethylolpropane tris-[3-(bis(2,4,6-trimethylbenzoyl)phosphoryl)propanoate]

A solution of HP(COMes)$_2$ (3.031 g, 9.29 mmol, 3 eq.) and NEt$_3$ (94 μL, 0.93 mmol, 0.3 eq.) in dme (30 ml) was prepared in a 100 ml Schlenk flask. After the addition of trimethylolpropane triacrylate (0.834 mL, 3.10 mmol, 1 eq.), the solution was stirred at room temperature for 12 h. A solution of HCl in diethyl ether (0.5 ml, 0.93 mmol, 0.3 eq.) and the reaction mixture stirred for 1 h at room temperature. The solvent was removed under vacuum, toluene (15 ml) was added and the precipitate of triethylammonium chloride was separated by filtration. After the addition of aqueous hydrogen peroxide (3.2 mL, 30.66 mmol, 3.3 eq., 30 wt.-%) at 0° C., the reaction mixture was stirred at room temperature for 12 h. The solvent was removed in vacuo, the residual solid was dissolved in diethyl ether (50 mL) and dried over NaSO$_4$. After filtration, the solvent was removed under reduced pressure to obtain a yellow solid (3.531 g, 2.70 mmol, 87%, M=1309.39 g/mol).

$^{31}$P{$^{1}$H} NMR (121.49 MHz, C$_6$D$_6$, 298 K): δ=26.62 ppm; UV/VIS λ [nm]=240 (sh.), 291, 362, 394; IR ν [cm$^{-1}$]=; ESI MS [M+NH$_4$]$^+$ m/z=1340.5753, meas. 1340.5735; m.p. 79° C.

25b) A mixture of trimethylolpropane tris-[3-(bis(2,4,6-trimethylbenzoyl)-phosphoryl)-propanoate], trimethylolpropane monoacrylate-bis-[3-(bis(2,4,6-trimethylbenzoyl)-phosphoryl)-propanoate] and trimethylolpropane bisacrylate-mono-[3-(bis(2,4,6-trimethylbenzoyl)-phosphoryl)-propanoate]

A solution of HP(COMes)$_2$ (150 mg, 0.460 mmol, 1.5 eq.) and NEt$_3$ (7 μL, 0.05 mmol, 0.15 eq.) in 1,2-dimethoxyethane (dme, 1.5 ml) was prepared in a 100 ml Schlenk flask. After the addition of trimethylolpropane triacrylate (82 μL, 0.306 mmol, 1 eq.), the solution was stirred at room temperature for 12 h. A solution of HCl in diethyl ether (25 μl, 0.05 mmol, 0.15 eq.) and the reaction mixture stirred for 1 h at room temperature. The solvent was removed under vacuum, toluene (1.5 ml) was added and the precipitate of triethylammonium chloride was separated by filtration. The solvent was removed in vacuo, the residual solid was dissolved in dme (3 mL) and dry air was passed through the solution for 20 min before stirring the solution for 3 h at room temperature. After removal of the solvent under reduced pressure the yellow solid residue was dried under high vacuum for 2 h to obtain the desired product mixture (243 mg, 93%).

$^{31}$P NMR (101.3 MHz, thf, 298 K): δ=25.22, 25.26, 25.38 ppm.

26) Dimethyl 2-(bis(2,4,6-trimethylbenzoyl)phosphino)fumarate and dimethyl 2-(bis(2,4,6-trimethylbenzoyl)phosphino)maleate In an NMR tube HP(COMes)$_2$ (21 mg, 0.064 mmol, 1 eq.) was dissolved in dme (0.5 mL). Triethylamine (1 μL, 11 mol-%) and dimethyl acetylene dicarboxylate (7.9 μL, 0.064 mmol, 1 eq.) were added to the solution. After mixing for 30 min a $^{31}$P NMR spectrum was recorded.

$^{31}$P NMR (121.49 MHz, dme, 298 K) δ[ppm]=56.93 (d, $^3J_{PH(cis)}$=21.87 Hz) and 59.72 (d, $^3J_{PH(trans)}$=14.58 Hz)

27) 3-(bis(2,4,6-trimethylbenzoyl)phosphoryl)propanoyl-oxyethyltrimethylammonium chloride

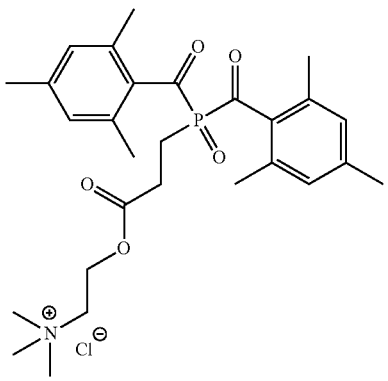

In a 100 mL Schlenk flask HP(COMes)$_2$ (1.19 g, 3.65 mmol, 1 eq.) was suspended in degassed, destilled water (10 mL). NEt$_3$ (50 μL, 0.365 mmol, 0.1 eq.) followed by 2-acryloxyethyltrimethylammonium chloride (1 mL, 3.65 mmol, 1 eq., 80 wt.-% in water) was added to the suspension. The flask was first kept in a ultra-sound bath at 40° C. for 2 h. Subsequently, the reaction mixture was allowed to stir at room temperature for 12 h. Aqueous concentrated hydrochloric acid (33 μL, 0.1 eq., 37 wt.-%) was added to adjust the pH to around 5 to 6. After the addition of aq. hydrogen peroxide (0.38 mL, 3.65 mmol, 1 eq., 30 wt.-%) at 0° C., the reaction mixture was stirred at room temperature for 12 h. The obtained yellow precipitate was collected by filtration and dried under high vacuum for 4 h (first fraction, 0.359 g, 18%). The remaining solution was concentrated in vacuo and the residual solid was recrystallised from ethanol. A yellow solid was obtained (second fraction, 1.17 g, 60%, M=536.04 g/mol). Total yield: 78%.

$^{31}$P{$^1$H} NMR (101.3 MHz, H$_2$O, 298K): 25.33 ppm.

Examples 28 to 31: Emulsion Polymerisations and Bulk Polymerisations

Bulk Polymerisations (BP)

A solution of the photoinitiator (PI) (0.1 mol-%) in the monomer (styrene (S), vinyl acetate (VA)) was prepared in a degas sed quartz tube sealed with a septum. The sample was irradiated with UV light under vigorous stirring for 1.5 h at room temperature. The obtained polymers were washed with methanol and dried under high vacuum for 1 h.

Emulsion Polymerisations (EP)

In a quartz tube sealed with septum 12 mL degassed SDS solution (1.7 weight-%) and the (PI 0.14 mol-%) were mixed. Subsequently, the monomer was added and the suspension was stirred vigorously for 15 min. The sample was irradiated with UV light for 1.5 h, before precipitating the polymer with methanol.

UV irradiation was carried out for all examples 28 to 31 with a mercury vapour pressure lamp (Heraeus TQ 150, 150 W) inside a quartz dip tube, which was immersed into a temperature controlled solvent bath.

Results:

| Example | PI according to Example | M (PI) [mg] | Monomer | V (monomer) [mL] | Yield [%] |
|---|---|---|---|---|---|
| 28 (EP) | 7a | 10.8 | S | 2 | 74.7 |
| 29 (EP) | 4c | 11.4 | S | 2 | 84.7 |
| 30 (BP) | 5b | 14.5 | VA | 3 | 63.6 |
| 31 (BP) | 8b | 26.9 | VA | 3 | 77.6 |

The polymer of Example 29 was not soluble in chloroform of DMF and could therefore not be characterised by size exclusion chromatography (SEC).

Examples 32 to 34: Emulsion Polymerisations

The given amount of photoinitiator was mixed with degas sed, distilled water (10 mL for the surfactant free emulsion polymerization, SFEP) or SDS-solution (2 mL, 10 wt-%) and styrene (1 ml) in a 15 mL glass vial. The obtained suspension was stirred vigorously for 15 min prior to irradiation. The mixture was subsequently irradiated with blue LED light for 1.5 h whilst stirring, to yield a polystyrene dispersion in water. Irradiation experiments with blue LED light were performed in the cavity of an aluminium cylinder (d=12 cm, h=25 cm) fitted with a 5 m self-adhesive LED strip ($\lambda_{max}$=465 nm, 60 LEDs per meter) connected to a power-supply unit.

Results:

| Example | PI according to Example | M (PI) [mg] | Result: |
|---|---|---|---|
| 32 (SDS) | 18 | 11.2 (1.23 wt.-%) | White polystyrene latex |
| 33 (SDS) | 19b | 11.5 (1.49 wt.-% | White polystyrene latex |
| 34 (SFEP) | 23 | 149 (16.4 wt.-%) | White polystyrene latex, DLS: $Z_{av}$ = 127 nm, PDI = 0.19 |

DLS = Dynamic Light Scattering,
PDI = Polydispersity Index

Examples 35 to 39: Bulk Polymerisations

The photoinitiator (PI) was dissolved in the monomer (n-butylacrylate, BA or 1,6-hexandioldiacrylate, HDDA) and the solution was transferred to a round glass dish such that the bottom of the dish was covered by the liquid. The mixture was subsequently irradiated from above at room temperature with a mercury vapour lamp (Heraeus TQ 150, 150 W) inside a quartz dip tube, which was immersed into a temperature controlled solvent bath for 1.5 h (Example 39: 2 h).
Results:

| Example | PI according to Example | M (PI) [mg] | Monomer M | V (M) [mL] | Polymer Characterisation |
|---|---|---|---|---|---|
| 35 | 25a | 42 (2.5 wt-%) | BA | 1.5 | gel like colourless polymer, swellable in thf |
| 36 | 14b | 19.7 (1.76 wt-%) | BA | 1.5 | gel like colourless polymer, insoluble in thf |
| 37 | 15b | 42 (2.5 wt-%) | BA | 1.5 | gel like colourless polymer, swellable in thf |
| 38 | 25b | 42 (2.5 wt-%) | BA | 1.5 | rubber like, colourless polymer, insoluble in thf |
| 39 | 25a | 30 (0.59 wt-%) | HDDA | 5 | Solid, brittle, colourless polymer, insoluble in thf |

Examples 40 and 41: Solution Polymerisations

A solution of the monomer (1.5 mL) and the photoinitiator (PI) in the solvent was prepared in a 15 mL glass vial sealed with a septum, under an argon atmosphere. The solution was irradiated with blue LED light as described for examples 32 to 34 for 2 hours (ex. 40) or 1.5 hours (ex. 41) whilst stirring.
Results:

| Example | PI according to Example | M (PI) [mg] | Monomer M | V(M) [mL] | Solvent | Polymer Characterisation |
|---|---|---|---|---|---|---|
| 40 | 23 | 42 (2.5 wt-%) | BA | 1.5 | dme (2 ml) | gel like colourless polymer |
| 41 | 27 | 42 (2.5 wt-%) | AETMACL | 2.3 | water (5 ml) | water soluble polymer |

AETMACL: 2-acryloxy-ethyltri-methyl-ammonium chloride (80% in $H_2O$)

The present invention is not limited to embodiments described herein; reference should be had to the appended claims.

What is claimed is:
1. A process for the preparation of compounds of formula (I):

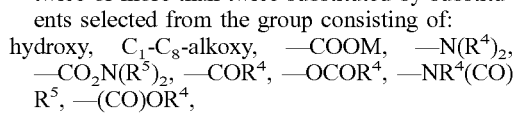

(I)

wherein,
n is an integer from 2 to 6
m is 1 or 2,
$R^1$ is a substituent of formula (IIe)

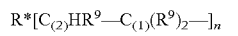

(IIe)

wherein, in formula (IIe),
R* is
a n-valent substituent selected from the group consisting of heteroaryl-n-yl and $R^{10}(\text{-Het-}(C=O)-)_n$, wherein Het independently is either O or $NR^4$ and $R^{10}$ is alkane-n-yl, alkene-n-yl or aryl-n-yl and wherein the carbonyl carbons are bound to the $C_{(2)}$ carbon atoms, wherein, the aforementioned alkane-n-yl and alkene-n-yl substituents of $R^{10}$ are
either not, once, twice or more than twice interrupted by non-successive functional groups selected from the group consisting of:
—O—, —$NR^4$—, —CO—, —O(CO)—, —(CO)O—, $NR^4$(CO)—, —(CO)$NR^4$—,
and,
either not, additionally or alternatively either once, twice or more than twice interrupted by aryldiyl,
and,
either not, additionally or alternatively either once, twice or more than twice substituted by substituents selected from the group consisting of:
hydroxy, $C_1$-$C_8$-alkoxy, —COOM, —N($R^4$)$_2$, —$CO_2$N($R^5$)$_2$, —$COR^4$, —$OCOR^4$, —$NR^4$(CO) $R^5$, —(CO)$OR^4$,
(1) and (2) indicate the numeration of the carbon atom, wherein each of the n $C_{(1)}$ carbon atoms is bonded to the central phosphorous atom depicted in formula (I) via the bond "-" shown on the right side of the bracket, and
$R^9$ independently of each other are hydrogen, alkyl, alkenyl or aryl or two substituents $R^9$ irrespective of whether they are both bound to $C_{(2)}$ or not are together alkanediyl or alkenediyl, wherein, the aforementioned alkyl, alkenyl, alkane-n-yl and alkene-n-yl substituents of $R^9$ are
either not, once, twice or more than twice interrupted by non-successive functional groups selected from the group consisting of:
—O—, —S—, —$SO_2$—, —SO—, —$SO_2NR^4$—, $NR^4SO_2$—, —$NR^4$—, —CO—, —O(CO)—, (CO)O—, —O(CO)O—, —$NR^4$(CO)$NR^4$—, $NR^4$(CO)—, —(CO)$NR^4$—, —$NR^4$(CO)O—, —O(CO)$NR^4$—, —Si($R^5$)$_2$—, —OSi($R^5$)$_2$—, —OSi($R^5$)$_2$O—, —Si($R^5$)$_2$O—,
and,
either not, additionally or alternatively either once, twice or more than twice interrupted by bivalent residues selected from the group consisting of heterocyclo-diyl, and aryldiyl,
and
either not, additionally or alternatively either once, twice or more than twice substituted by substituents selected from the group consisting of:
oxo, hydroxy, halogen, cyano, azido, $C_6$-$C_{14}$-aryl, $C_1$-$C_8$-alkoxy, $C_1$-$C_8$-alkylthio, —$SO_3M$, —COOM, $PO_3M_2$, $-PO(N(R^5)_2)_2$, $PO(OR^5)_2$, $-SO_2N(R^4)_2$, $-N(R^4)_2$, $-N(R^4)_3{}^+An^-$, $-CO_2N(R^5)_2$, $-COR^4$, $-OCOR^4$, $-NR^4(CO)R^5$, $-(CO)OR^4$, $-NR^4(CO)N(R^4)_2$, $-Si(OR^5)_y$ $(R^5)_{3-y}$, $-OSi(OR^5)_y(R^5)_{3-y}$ with y=1, 2 or 3, $R^2$ and $R^3$ are independently of each other aryl or heterocyclyl, alkyl or alkenyl, wherein, the aforementioned alkyl and alkenyl substituents of $R^2$ and $R^3$ are either not, once, twice or more than twice interrupted by non-successive functional groups selected from the group consisting of:
—O—, —$NR^4$—, —CO—, —OCO—, —O(CO)O—, $NR^4(CO)$—, —$NR^4(CO)O$—, O(CO)$NR^4$—, —$NR^4(CO)NR^4$—,
and, either not, additionally or alternatively either once, twice or more than twice interrupted by bivalent residues selected from the group consisting of heterocyclo-diyl, and aryldiyl, and either not, additionally or alternatively either once, twice or more than twice substituted by substituents selected from the group consisting of:
oxo, hydroxyl, halogen, cyano, $C_6$-$C_{14}$-aryl; heterocyclyl, $C_1$-$C_8$-alkoxy, $C_1$-$C_8$-alkylthio, —COOM, —$SO_3M$, —$PO_3M_2$, —$SO_2N(R^4)_2$, —$NR^4SO_2R^5$, —$N(R^4)_2$—, —$N^+(R^4)_3An^-$, —$CO_2N(R^4)_2$, —$COR^4$—, —$OCOR^5$, —$O(CO)OR^5$, $NR^4(CO)R^4$, —$NR^4(CO)OR^4$, $O(CO)N(R^4)_2$, —$NR^4(CO)N(R^4)_2$, wherein, in all formulae where used $R^4$ is independently selected from the group consisting of hydrogen, $C_1$-$C_8$-alkyl, $C_6$-$C_{14}$-aryl, and heterocyclyl or $N(R^4)_2$ as a whole is a N-containing heterocycle, $R^5$ is independently selected from the group consisting of $C_1$-$C_8$-alkyl, $C_6$-$C_{14}$-aryl, and heterocyclyl or $N(R^5)_2$ as a whole is a N-containing heterocycle, M is hydrogen, or 1/q equivalent of an q-valent metal ion or is an ammonium ion or a guanidinium ion or a primary, secondary, tertiary or quarternary organic ammonium ion, and $An^-$ is 1/p equivalent of a p-valent anion, wherein "aryl" denotes carbocyclic aromatic substituents, the carbocyclic, aromatic substituents being unsubstituted, or being substituted by up to five identical or different substituents per cycle, the process comprising at least the step of reacting compounds of formula (III)

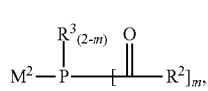   (III)

with compounds of formula (IVe), $R^*[R^9C_{(2)}=C_{(1)}(R^9)_2]_n$   (IVe), wherein, in formula (IVe), (1), (2), $R^2$, $R^3$, $R^9$, $R^*$, n and m have the same meaning as described for formulae (I) and (IIe) above, and wherein, in formula (II), $M^2$ is hydrogen, or 1/q equivalent of an q-valent metal ion or is an ammonium ion or a heterocyclium cation, a guanidinium ion or a primary, secondary, tertiary or quarternary organic ammonium ion, and wherein the reaction if $M^2$ is hydrogen is carried out in the presence of a base.

2. The process as recited in claim 1, wherein if $M^2$ is 1/q equivalent of an q-valent metal ion or a quarternary organic ammonium ion or a heterocyclylium cation, an acid or an aqueous reference system is added after the reaction to protonate intermediates.

3. The process as recited in claim 1, wherein, in compounds of formulae (I) and (III), m is 1 or 2, and $R^2$ is $C_6$-$C_{14}$-aryl or heterocyclyl, or is $C_1$-$C_{18}$-alkyl or $C_2$-$C_{18}$-alkenyl, wherein, the aforementioned substituents $C_1$-$C_{18}$-alkyl or $C_2$-$C_{18}$-alkenyl of $R^2$ are either not, once, twice or more than twice interrupted by non-successive functional groups selected from the group consisting of:
—O—, —$NR^4$—, —$N^+(R^4)_2An^-$-, —CO—, $NR^4(CO)$—, —$NR^4(CO)O$—, $(CO)NR^4$—, and which is not, additionally or alternatively either once, twice or more than twice substituted by substituents selected from the group consisting of:
halogen, cyano, $C_6$-$C_{14}$-aryl; heterocyclyl, $C_1$-$C_8$-alkyl, $C_1$-$C_8$-alkoxy, $C_1$-$C_8$-alkylthio, $C_2$-$C_8$-alkenyl, $C_4$-$C_{15}$-arylalkyl, —COOM, $SO_2N(R^3)_2$—, $N(R^4)_2$—, —$N^+(R^4)_3An^-$, —$CO_2N(R^4)_2$, wherein, $R^4$ is independently selected from the group consisting hydrogen, $C_1$-$C_8$-alkyl, $C_6$-$C_{14}$-aryl, $C_7$-$C_{15}$-arylalkyl and heterocyclyl or $N(R^4)_2$ as a whole is a N-containing heterocycle or $N^+(R^4)_2An^-$ and $N^+(R^4)_3An^-$ as a whole is or contains a cationic N-containing heterocycle with a counteranion, $R^5$ is independently selected from the group consisting $C_1$-$C_8$-alkyl, $C_6$-$C_{14}$-aryl, $C_7$-$C_{15}$-arylalkyl and heterocyclyl or $N(R^5)_2$ as a whole is a N-containing heterocycle or $N^+(R^5)_2An^-$ and $N^+(R^5)_3An^-$ as a whole is or contains a cationic N-containing heterocycle with a counteranion, M is hydrogen, lithium, sodium, potassium, one half equivalent of calcium, zinc or iron (II), or one third equivalent of aluminium (III) or is an ammonium ion or a primary, secondary, tertiary or quarternary organic ammonium ion, and $An^-$ is 1/p equivalent of an p-valent anion.

4. The process as recited in claim 1, wherein, m is 2, and $R^2$ is $C_6$-$C_{14}$-aryl.

5. The process as recited in claim 1, wherein the process is carried out in water.

6. Compounds of formula (I) of claim 1:

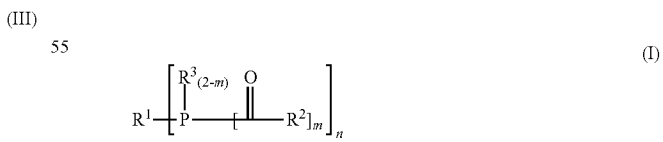   (I)

wherein, n is an integer from 2 to 6 m is 1 or 2, $R^1$ is a substituent of formula (IIe)

   (IIe)

wherein, in formula (IIe),

R* is
a n-valent substituent selected from the group consisting of heteroaryl-n-yl and $R^{10}(-\text{Het-}(C=O)-)_n$, wherein Het independently is either O or $NR^4$ and $R^{10}$ is alkane-n-yl, alkene-n-yl or aryl-n-yl and wherein the carbonyl carbons are bound to the $C_{(2)}$ carbon atoms, wherein, the aforementioned alkane-n-yl and alkene-n-yl substituents of $R^{10}$ are either not, once, twice or more than twice interrupted by non-successive functional groups selected from the group consisting of:
—O—, —$NR^4$—, —CO—, —O(CO)—, —(CO)O—, $NR^4$(CO)—, —(CO)$NR^4$—,
and, either not, additionally or alternatively either once, twice or more than twice interrupted by aryldiyl,
and, either not, additionally or alternatively either once, twice or more than twice substituted by substituents selected from the group consisting of:
hydroxy, $C_1$-$C_8$-alkoxy, —COOM, —N($R^4$)$_2$, —CO$_2$N($R^5$)$_2$, —COR$^4$, —OCOR$^4$, —$NR^4$(CO)R$^5$, —(CO)OR$^4$, (1) and (2) indicate the numeration of the carbon atom, wherein each of the n $C_{(1)}$ carbon atoms is bonded to the central phosphorous atom depicted in formula (I) via the bond "-" shown on the right side of the bracket, and $R^9$ independently of each other are hydrogen, alkyl, alkenyl or aryl or two substituents $R^9$ irrespective of whether they are both bound to $C_{(2)}$ or not are together alkanediyl or alkenediyl, wherein, the aforementioned alkyl, alkenyl, alkane-n-yl and alkene-n-yl substituents of $R^9$ are either not, once, twice or more than twice interrupted by non-successive functional groups selected from the group consisting of:
—O—, —S—, —SO$_2$—, —SO—, —SO$_2$NR$^4$—, NR$^4$SO$_2$—, —NR$^4$—, —CO—, —O(CO)—, (CO)O—, —O(CO)O—, —NR$^4$(CO)NR$^4$—, NR$^4$(CO)—, —(CO)NR$^4$—, —NR$^4$(CO)O—, —O(CO)NR$^4$—, —Si(R$^5$)$_2$—, —OSi(R$^5$)$_2$—, —OSi(R$^5$)$_2$O—, —Si(R$^5$)$_2$O—,
and, either not, additionally or alternatively either once, twice or more than twice interrupted by bivalent residues selected from the group consisting of heterocyclo-diyl, and aryldiyl,
and either not, additionally or alternatively either once, twice or more than twice substituted by substituents selected from the group consisting of:
oxo, hydroxy, halogen, cyano, azido, $C_6$-$C_{14}$-aryl, $C_1$-$C_8$-alkoxy, $C_1$-$C_8$-alkylthio, —SO$_3$M, —COOM, PO$_3$M$_2$, —PO(N(R$^5$)$_2$)$_2$, PO(OR)$_2$, —SO$_2$N(R$^4$)$_2$, —N(R$^4$)$_2$, —N(R$^4$)$_3$$^+$An$^-$, —CO$_2$N(R$^5$)$_2$, —COR$^4$, —OCOR$^4$, —NR$^4$(CO) R$^5$, —(CO)OR$^4$, —NR$^4$(CO)N(R$^4$)$_2$, —Si(OR$^5$)$_y$ (R$^5$)$_{3-y}$, —OSi(OR$^5$)$_y$(R$^5$)$_{3-y}$ with y=1, 2 or 3, $R^2$ and $R^3$ are independently of each other aryl or heterocyclyl, alkyl or alkenyl, wherein, the aforementioned alkyl and alkenyl substituents of $R^2$ and $R^3$ are either not, once, twice or more than twice interrupted by non-successive functional groups selected from the group consisting of:
—O—, —NR$^4$—, —CO—, —OCO—, —O(CO) O—, NR$^4$(CO)—, —NR$^4$(CO)O—, O(CO) NR$^4$—, —NR$^4$(CO)NR$^4$—,
and, either not, additionally or alternatively either once, twice or more than twice interrupted by bivalent residues selected from the group consisting of heterocyclo-diyl, and aryldiyl,
and either not, additionally or alternatively either once, twice or more than twice substituted by substituents selected from the group consisting of:
oxo, hydroxyl, halogen, cyano, $C_6$-$C_{14}$-aryl; heterocyclyl, $C_1$-$C_8$-alkoxy, $C_1$-$C_8$-alkylthio, —COOM, —SO$_3$M, —PO$_3$M$_2$, —SO$_2$N(R$^4$)$_2$, —NR$^4$SO$_2$R$^5$, —N(R$^4$)$_2$—, —N$^+$(R$^4$)$_3$An$^-$, —CO$_2$N(R$^4$)$_2$, —COR$^4$—, —OCOR$^5$, —O(CO) OR$^5$, NR$^4$(CO)R$^4$, —NR$^4$(CO)OR$^4$, O(CO)N (R$^4$)$_2$, —NR$^4$(CO)N(R$^4$)$_2$, wherein, in all formulae where used
$R^4$ is independently selected from the group consisting of hydrogen, $C_1$-$C_8$-alkyl, $C_6$-$C_{14}$-aryl, and heterocyclyl or N(R$^4$)$_2$ as a whole is a N-containing heterocycle,
$R^5$ is independently selected from the group consisting of $C_1$-$C_8$-alkyl, $C_6$-$C_{14}$-aryl, and heterocyclyl or N(R$^5$)$_2$ as a whole is a N-containing heterocycle,
M is hydrogen, or 1/q equivalent of an q-valent metal ion or is an ammonium ion or a guanidinium ion or a primary, secondary, tertiary or quarternary organic ammonium ion,
and
An$^-$ is 1/p equivalent of a p-valent anion,
wherein "aryl" denotes carbocyclic aromatic substituents, the carbocyclic, aromatic substituents being unsubstituted, or being substituted by up to five identical or different substituents per cycle.

7. Compounds as recited in claim 6, wherein the compounds are:
trimethylolpropane tris[3-(bis(2,4,6-trimethylbenzoyl) phosphino) propanoate], and
trimethylolpropane monoacrylate bis-[3-(bis(2,4,6-trimethylbenzoyl)phosphino) propanoate].

8. Compounds of formula (V)

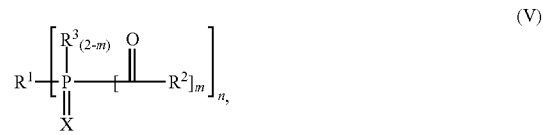

(V)

wherein,
$R^1$, $R^2$, $R^3$, n and m have the meaning as recited for formula (I) of claim 1, and
X is oxygen or sulphur.

9. The compounds as recited in claim 8, wherein the compounds are:
trimethylolpropane tris-[3-(bis(2,4,6.trimethylbenzoyl) phosphoryl) propanoate], and
trimethylolpropane monoacrylate bis-[3-(bis(2,4,6.trimethylbenzoyl)phosphoryl) propanoate].

* * * * *